(12) United States Patent
Huang et al.

(10) Patent No.: US 12,105,079 B2
(45) Date of Patent: Oct. 1, 2024

(54) BIOLOGICAL NANOPORES HAVING TUNABLE PORE DIAMETERS AND USES THEREOF AS ANALYTICAL TOOLS

(71) Applicant: Rijksuniversiteit Groningen, Groningen (NL)

(72) Inventors: Gang Huang, Beijing (CN); Giovanni Maglia, Glimmen (NL)

(73) Assignee: Rijksuniversiteit Groningen, Groningen (NL)

(*) Notice: Subject to any disclaimer, the term of this patent is extended or adjusted under 35 U.S.C. 154(b) by 756 days.

(21) Appl. No.: 17/269,771

(22) PCT Filed: Sep. 11, 2019

(86) PCT No.: PCT/NL2019/050588
§ 371 (c)(1),
(2) Date: Feb. 19, 2021

(87) PCT Pub. No.: WO2020/055246
PCT Pub. Date: Mar. 19, 2020

(65) Prior Publication Data
US 2021/0325365 A1    Oct. 21, 2021

(30) Foreign Application Priority Data
Sep. 11, 2018    (EP) .................................... 18193722

(51) Int. Cl.
*G01N 33/487*    (2006.01)
*C07K 14/435*    (2006.01)
*G01N 27/447*    (2006.01)

(52) U.S. Cl.
CPC .  *G01N 33/48721* (2013.01); *C07K 14/43595* (2013.01); *G01N 27/44791* (2013.01);
(Continued)

(58) Field of Classification Search
None
See application file for complete search history.

(56) References Cited

U.S. PATENT DOCUMENTS

| 5,795,782 A | 8/1998 | Church et al. |
| 6,015,714 A | 1/2000 | Baldarelli et al. |

(Continued)

FOREIGN PATENT DOCUMENTS

| CN | 104710519 A | 6/2015 |
| CN | 112480204 A | 3/2021 |

(Continued)

OTHER PUBLICATIONS

B.H. Balakrishna, et al., "Binding of a pleurotolysin ortholog from Pleurotus eryngii to sphingomyelin and cholesterol-rich membrane domains", Journal of Lipid Research, 54(10): p. 2933-2943, Oct. 2013.*

(Continued)

*Primary Examiner* — J. Christopher Ball
(74) *Attorney, Agent, or Firm* — Wilson Sonsini Goodrich & Rosati

(57) ABSTRACT

The invention relates to the field of nanopores, in particular to engineered Fragaceatoxin C (FraC) nanopores and their application in analyzing biopolymers and other (biological) compounds, such as single-molecule (protein) sequencing. Provided is a system comprising oligomeric FraC nanopores comprised in a lipid bilayer, wherein the sum of the nanopore fraction in the heptameric (Type II) state and the nanopore fraction in the hexameric (Type III) state represents at least 60% of the total number of FraC nanopores.

Figure 1A:
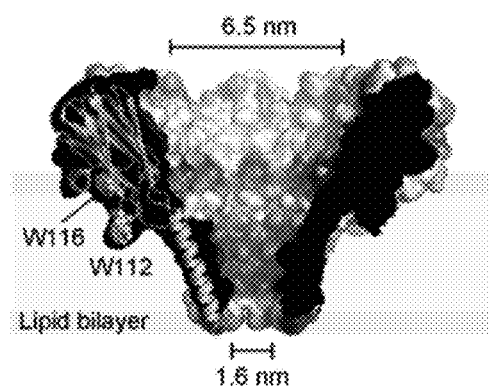

24 Claims, 16 Drawing Sheets
Specification includes a Sequence Listing.

(52) U.S. Cl.
CPC ...... *C07K 2319/03* (2013.01); *C07K 2319/21* (2013.01); *C07K 2319/22* (2013.01)

(56) References Cited

U.S. PATENT DOCUMENTS

| | | | |
|---|---|---|---|
| 6,267,872 | B1 | 7/2001 | Akeson et al. |
| 6,362,001 | B1 | 3/2002 | Cai et al. |
| 6,362,002 | B1 | 3/2002 | Denison et al. |
| 6,428,959 | B1 | 8/2002 | Deamer |
| 6,464,842 | B1 | 10/2002 | Golovchenko et al. |
| 6,465,946 | B1 | 10/2002 | Yoon et al. |
| 6,617,113 | B2 | 9/2003 | Deamer |
| 6,627,067 | B1 | 9/2003 | Branton et al. |
| 6,673,615 | B2 | 1/2004 | Denison et al. |
| 6,746,594 | B2 | 6/2004 | Akeson et al. |
| 8,673,550 | B2 | 3/2014 | Gundlach et al. |
| 9,766,248 | B2 | 9/2017 | Lindsay et al. |
| 10,883,140 | B2 | 1/2021 | Church et al. |
| 10,900,067 | B2 | 1/2021 | Aksimentiev et al. |
| 11,312,755 | B2 | 4/2022 | Maglia et al. |
| 11,313,857 | B2 | 4/2022 | Wanunu et al. |
| 11,339,365 | B2 | 5/2022 | Nivala et al. |
| 11,391,693 | B2 | 7/2022 | Boyanov et al. |
| 11,703,476 | B2 | 7/2023 | Wanunu et al. |
| 2003/0104428 | A1 | 6/2003 | Branton et al. |
| 2004/0121525 | A1 | 6/2004 | Chopra et al. |
| 2008/0287656 | A1 | 11/2008 | Peters et al. |
| 2011/0174625 | A1 | 7/2011 | Akeson et al. |
| 2011/0193249 | A1 | 8/2011 | Chen et al. |
| 2011/0311965 | A1 | 12/2011 | Maglia et al. |
| 2012/0055792 | A1 | 3/2012 | Gundlach et al. |
| 2012/0107802 | A1 | 5/2012 | Stoddart et al. |
| 2016/0032235 | A1 | 2/2016 | Segard |
| 2020/0123594 | A1 | 4/2020 | Rothberg et al. |
| 2020/0348307 | A1 | 11/2020 | Beierle et al. |
| 2021/0189482 | A1 | 6/2021 | Akeson et al. |
| 2021/0340192 | A1 | 11/2021 | Nivala |
| 2022/0091093 | A1 | 3/2022 | Wanunu et al. |
| 2022/0242922 | A1 | 8/2022 | Maglia et al. |
| 2022/0277814 | A1 | 9/2022 | Nivala |
| 2022/0283140 | A1 | 9/2022 | Wanunu et al. |
| 2022/0299469 | A1 | 9/2022 | Boyanov et al. |
| 2022/0396758 | A1 | 12/2022 | Nivala et al. |
| 2022/0412948 | A1 | 12/2022 | Maglia et al. |
| 2023/0048421 | A1 | 2/2023 | Zhang et al. |
| 2023/0220002 | A1 | 7/2023 | Long et al. |
| 2023/0221296 | A1 | 7/2023 | Long et al. |

FOREIGN PATENT DOCUMENTS

| | | |
|---|---|---|
| CN | 112500459 A | 3/2021 |
| EP | 2350122 A1 | 8/2011 |
| EP | 2978773 A1 | 2/2016 |
| EP | 2814939 B1 | 4/2018 |
| EP | 3485029 A1 | 5/2019 |
| EP | 3598133 A1 | 1/2020 |
| EP | 4070092 B1 | 8/2023 |
| JP | 2013540423 A | 11/2013 |
| WO | WO-0079257 A1 | 12/2000 |
| WO | WO-2005124888 A1 | 12/2005 |
| WO | WO-2006028508 A2 | 3/2006 |
| WO | WO-2009020682 A2 | 2/2009 |
| WO | WO-2010004265 A1 | 1/2010 |
| WO | WO-2010034018 A2 | 3/2010 |
| WO | WO-2010055307 A1 | 5/2010 |
| WO | WO-2010082860 A1 | 7/2010 |
| WO | WO-2013123379 A2 | 8/2013 |
| WO | WO-2014153625 A1 | 10/2014 |
| WO | WO-2014190299 A2 | 11/2014 |
| WO | WO-2015040423 A1 | 3/2015 |
| WO | WO-2016166232 A1 | 10/2016 |
| WO | WO-2018012963 A1 | 1/2018 |
| WO | WO-2020055246 A1 | 3/2020 |
| WO | WO-2020160559 A1 | 8/2020 |
| WO | WO-2021021592 A1 | 2/2021 |
| WO | WO-2021101378 A1 | 5/2021 |
| WO | WO-2021111125 A1 | 6/2021 |
| WO | WO-2022020461 A1 | 1/2022 |
| WO | WO-2023055246 A1 | 4/2023 |

OTHER PUBLICATIONS

Accession No. XP-002796191 Database UniProt (2009).

Beloimio A. et al., "Purification, cloning and characterization of fragaceatoxin C, a novel actinoporin from the sea anemone Actinia fragacea", Toxicon, Nov. 1, 2009 Elmsford, NY, US-ISSN 004100101, vol. 54, Nr:6, pp. 869-880.

Wloka, C. et al., "Alpha-Helical Fragaceatoxin C Nanopore Engineered for Double-Stranded and Single-Stranded Nucleic Acid Analysis", Angewandte Chemie, vol. 55, Nr. 40 (2016) pp. 12494-12498.

Mechaly, A. et al., "Structural Insights into the Oligomerization and Architecture of Eukaryotic Membrane Pore-Forming Toxins", Structure; vol. 19, No. 2 (2010) pp. 181-191.

Macrander, J. et al., "Evolution of the Cytolytic Pore-Forming Proteins (Actinoporins) in Sea Anemones", Toxins; vol. 8, No. 12 (2016) pp. 1-16.

Furini, S. et al., "Model-Based Prediction of the α-Hemolysin Structure in the Hexameric State", Biophysical Journal, vol. 95, No. 5 (2008) pp. 2265-2274.

Afshar Bakshloo, Mazdak, et al., Nanopore-Based Protein Identification. Journal of the American Chemical Society 144(6):2716-2725 (2022).

Akeson, M, et al., Microsecond time-scale discrimination among polycytidylic acid, polyadenylic acid, and polyuridylic acid as homopolymers or as segments within single RNA molecules. Biophysical Journal 77(6):3227-3233 (1999).

Akopian, Tatos, et al., Processive Degradation of Proteins and Other Catalytic Properties of the Proteasome From Thermoplasma Acidophilum. The Journal of biological chemistry 272(3):1791-1798 (1997).

Aksoyoglu, Alphan, et al., Size-dependent forced PEG partitioning into channels: VDAC, OmpC, and α-hemolysin. Proc Natl Acad Sci U S A 113(32):9003-9008 (2016).

Alfaro, Javier Antonio et al., The Emerging Landscape of Single-molecule Protein Sequencing Technologies. Nature Methods 18:604-617 (2021).

An, Na, et al., Single-molecule investigation of G-quadruplex folds of the human telomere sequence in a protein nanocavity. Proceedings of the National Academy of Sciences of the United States of America 111(40):14325-14331 (2014).

Anderluh, Gregor et al.: Cytolytic peptide and protein toxins from sea anemones (*Anthozoa: actiniaria*). Toxicon 40(2):111-124 (2002).

André, Ingemar., et al., Prediction of the structure of symmetrical protein assemblies. Proc Natl Acad Sci U S A 104(45):17656-17661 (2007).

Aqvist, et al., Dipoles localized at helix termini of proteins stabilize charges. Proc Natl Acad Sci U S A 88(5):2026-2030 (1991).

Asandei, Alina, et al., Electroosmotic Trap Against the Electrophoretic Force Near a Protein Nanopore Reveals Peptide Dynamics During Capture and Translocation. ACS Applied Materials & Interfaces 8(20):13166-13179 (2016).

Baaken, Gerhard, et al., High-resolution size-discrimination of single nonionic synthetic polymers with a highly charged biological nanopore. ACS Nano 9(6):6443-6449 (2015).

Bacri, Laurent, et al., Discrimination of neutral oligosaccharides through a nanopore. Biochem Biophys Res Commun 412(4):561-564 (2011).

Bakrac, Biserka, et al., Molecular determinants of sphingomyelin specificity of a eukaryotic pore-forming toxin. Journal of Biological Chemistry 283(27):18665-18677 (2008).

Balakrishna, B.H. et al.: Binding of a pleurotolysin ortholog from Pleurotus eryngii to sphingomyelin and cholesterol-rich membrane domains. Journal of Lipid Research (2013).

Balijepalli, Arvind, et al., Theory of Polymer-nanopore Interactions Refined Using Molecular Dynamics Simulations. Journal of the American Chemical Society 135(18):7064-7072 (2013).

(56) References Cited

OTHER PUBLICATIONS

Baniandres; Pablo Martin et al.: Enzyme-less Nanopore Detection of Post-translational Modifications Within Long Polypeptides. Nature Nanotechnology 18:1335-1340 (2023).
Barkow, Sarah R, et al., Polypeptide translocation by the AAA+ ClpXP protease machine. Chemical Biology 16(6):605-612 (2009).
Barlic, Ariana, et al., Lipid Phase Coexistence Favors Membrane Insertion of Equinatoxin-II, a Pore-forming Toxin from Actinia equina. Journal of Biological Chemistry 279(33):34209-34216 (2004).
Bayat, Parisa et al., Comprehensive Structural Assignment of Glycosaminoglycan Oligo and Polysaccharides by Protein Nanopore. Nature Communications. Vol. 13, No. 1 (2022): 12 pages.
Baytshtok, Vladimir, et al., A Structurally Dynamic Region of the HsLU Intermediate Domain Controls Protein Degradation and ATP Hydrolysis. Structure 24(10):1766-1777 (2016).
Becker, Samuel H, et al., Bacterial Proteasomes: Mechanistic and Functional Insights. Microbiology and Molecular Biology Reviews :MMBR 81(1):1-20 (2016).
Bell, Nicholas, Nanopores Formed by DNA Origami: A Review. FEBS letters 588(19):3564-3570 (2014).
Bellomio, Augusto, et al., Purification, Cloning and Characterization of Fragaceatoxin C, A Novel Actinoporin From the Sea Anemone Actinia Fragacea. Toxicon 54(6): 869-880 (2009).
Benaroudj, Nadia, et al., ATP hydrolysis by the proteasome regulatory complex PAN serves multiple functions in protein degradation. Molecular cell 1:69-78 (2003).
Beta-channel forming cytolysin—Bacillus cytotoxicus | UniProtKB | UniProt. Accession No. A0A2S1A9G3_9BACI in UniProt 2002-2024.
Bezrukov, S., et al., Dynamics and free energy of polymers partitioning into a nanoscale pore. Macromolecules 29, 8517-8522 (1996).
Biesemans, Annemie., et al., A Protein Rotaxane Controls the Translocation of Proteins Across a ClyA Nanopore. Nano Lett 15(9):6076-6081 (2015).
Boersma, Arnold J, et al., Continuous stochastic detection of amino acid enantiomers with a protein nanopore. Angewandte Chemie International Edition English 51(38):9606-9609 (2012).
Booner, Oscar, et al., Osmotic and Activity Coefficients of Sodium and Potassium Glutamate at 298.15 K. Journal of Chemical & Engineering Data 26:147-148 (1981).
Bouchnak, Imen, et al., Structure, function, and substrates of Clp AAA+ protease systems in cyanobacteria, plastids, and apicoplasts: A comparative analysis. Journal of Biological Chemistry 296:1-16 (2021).
Brauning, Bastian, et al., Structure and mechanism of the two-component α-helical pore-forming toxin YaxAB. Nature communications 9:1-14 (2018).
Brinkerhoff, Henry, et al., Multiple Rereads of Single Proteins at Single-amino Acid Resolution Using Nanopores. Science 374(6574):1509-1513 (2021).
Buchberger, Alexander, et al., Roles of Cdc48 in Regulated Protein Degradation in Yeast. Sub-cellular Biochemistry 66:195-222 (2013).
Burns, Jonathan, et al., Lipid-bilayer-spanning DNA nanopores with a bifunctional porphyrin anchor. Angewandte Chemie 52(46):12069-12072 (2013).
Butler, Tom Z, et al., Single-molecule DNA Detection With An Engineered MspA Protein Nanopore. Proceedings of the National Academy of Sciences of the United States of America 105(52):20647-20652 (2008).
Cao, Chan, et al., Discrimination of oligonucleotides of different lengths with a wild-type aerolysin nanopore. Nature Nanotechnology 11(8):713-718 (2016).
CAO; Chan et al.: Single-molecule sensing of peptides and nucleic acids by engineered aerolysin nanopores. Nature Communications 10: 4918 (2019).
Castanzo, Dominic, et al., The AAA+ ATPase Msp1 is a Processive Protein Translocase with Robust Unfoldase Activity. Proceedings of the National Academy of Sciences of the United States of America 117(26):14970-14977 (2020).

Chavis, Amy E, et al., Single Molecule Nanopore Spectrometry for Peptide Detection. ACS Sensors 2(9):1319-1328 (2017).
Chen, Baoyu, et al., Engagement of arginine finger to ATP triggers large conformational changes in NtrC1 AAA+ ATPase for remodeling bacterial RNA polymerase. Structure 18(11):1420-1430 (2010).
Chinappi, Mauro, et al., Analytical Model for Particle Capture in Nanopores Elucidates Competition Among Electrophoresis, Electroosmosis, and Dielectrophoresis. ACS Nano 14(11):15816-15828 (2020).
Chinappi, Mauro et al.: Protein sequencing via nanopore based devices: a nanofluidics perspective. Journal of Physics: Condensed Matter, Institute of Physics Publishing, Bristol, GB 30(20):204002 (2018), XP020327001. Doi: 10.1088/1361-648X/AABABE.
Clarke et al., Continuous base identification for single-molecule nanopore DNA sequencing. Nat Nanotechnol. 4(4):265-270 (2009).
Cressiot, Benjamin, et al., Dynamics and Energy Contributions for Transport of Unfolded Pertactin Through a Protein Nanopore. ACS Nano 9(9):9050-61 (2015).
Cressiot, Benjamin, et al., Protein Transport Through a Narrow Solid-state Nanopore at High Voltage: Experiments and Theory. American Chemical Society nano 6(7):6236-6243 (2012).
Cressiot, Benjamin, et al., Thermostable Virus Portal Proteins as Reprogrammable Adapters for Solid-state Nanopore Sensors. Nature Communications 9(4652): 1-7 (2018).
Crnković, Ana, et al., Biological Nanopores: Engineering on Demand. Life (Basel) 11(1):27 (2021).
Dal-Peraro, Matteo, et al., Pore-forming toxins: ancient, but never really out of fashion. Nature reviews. Microbiology 14(2):77-92 (2016).
DATABASE UniProt B9W5G6 XP002796191.
DELTA-Actitoxin-Aeq1b-like [Orbicella faveolata]. BioProject PRJNA381078, XP-020600665.1. (2017) https://www.ncbi.nlm.nih.gov/protein/1176123762?sat=4&satkey=191642050.
Derrington, Ian M, et al., Nanopore DNA sequencing with MspA. Proceedings of the National Academy of Sciences of the United States of America 107(37):16060-16065 (2010).
Derrington, Ian M. et al.: Subangstrom single-molecule measurements of motor proteins using a nanopore. Nature Biotechnology Sep. 28, 2015.
Dong, Changjiang et al.: The structure of Wza, the translocon for group 1 capsular polysaccharides in *Escherichia coli*, identifies a new class of outer membrane protein. Nature 444(7116):226-229 (2006). doi: 10.1038/nature05267.
Dong, Changjiang, et al., Wza the Translocon for *E. coli* Capsular Polysaccharides Defines a New Class of Membrane Protein. Nature 444:226-229 (2006).
Dougana, David, et al., AAA+ proteins and substrate recognition, it all depends on their partner in crime. FEBS Letters 529:6-10 (2002).
Effantin, Gregory, et al., Binding of the ClpA Unfoldase Opens the Axial Gate of ClpP Peptidase. The Journal of Biological Chemistry 285(19):14834-14840 (2010).
EP17734851.3 European Examination Report dated Feb. 12, 2020.
EP20206642.9 Extended European Search Report dated May 3, 2021.
Erlandson, Karl, et al., A Role for the Two-helix Finger of the Seca ATpase in Protein Translocation. Nature. Vol. 455, 7215:984-987 (2008).
European Patent Application No. EP22204590 European Extended Search Report dated Aug. 14, 2023.
Faller, Michael, et al., The structure of a mycobacterial outer-membrane channel. Science 303(5661):1189-1192 (2004).
Flynn, Julia, et al., Overlapping Recognition Determinants Within the ssrA Degradation Tag Allow Modulation of Proteolysis. Proceedings of the National Academy of Sciences of the United States of America 98(19):10584-10589 (2001).
Forouzan, Dara, et al., The Archaeal Proteasome is Regulated by a Network of AAA ATPases. The Journal of Biological Chemistry 287(46):39254-62 (2012).
Forster, Andreas et al.: The 1.9 Å structure of a proteasome-11S activator complex and implications for proteasome-PAN/PA700 interactions. Molecular Cell 18:589-599 (2005). DOI 10.1016/j.molcel.2005.04.016.

(56) References Cited

OTHER PUBLICATIONS

Franceschini, Lorenzo, et al., A nanopore machine promotes the vectorial transport of DNA across membranes. Nature Communications 4(2415): 8 Pages (2013).
Frees, Dorte, et al., Clp ATPases Are Required for Stress Tolerance, Intracellular Replication and Biofilm Formation in *Staphylococcus aureus*. Molecular Microbiology 54(5):1445-62 (2004).
Furini, Simone, et al., Model-based Prediction of the Alpha-hemolysin Structure in the Hexameric State. Biophysical journal 95 (5): 2265-2274 (2008).
García-Ortega, Lucia, et al., The Behavior of Sea Anemone Actinoporins at the Water-membrane Interface. Biochimica Et Biophysica Acta 1808 (9):2275-2288 (2011).
Gerega, Alexandra, et al., VAT, the Thermoplasma Homolog of Mammalian p97/VCP, Is an N Domain-regulated Protein Unfoldase. The Journal of Biological Chemistry 280(52):42856-42862 (2020).
Gimenez-Andres, Manuel, et al., The Many Faces of Amphipathic Helices. Biomolecules 8(45):1-14 (2018).
Glynn, Steven E, et al., Dynamic and Static Components Power Unfolding in Topologically Closed Rings of a AAA+ Proteolytic Machine. Nature Structural & Molecular Biology 19(6):616-622 (2012).
Gonzalez-Perez, Alfredo, et al., Biomimetic Triblock Copolymer Membrane Arrays: A Stable Template for Functional Membrane Proteins. Langmuir 25(18):10447-10450 (2009).
Gouaux, J.E. et al., Subunit stoichiometry of *Staphylococcal* alpha-hemolysin in crystals and on membranes: a heptameric transmembrane pore. Proceedings of the National Academy of Sciences of the United States of America 91(26): 12828-31 (1994).
Gu, Li-qun, et al., Electroosmotic Enhancement of the Binding of a Neutral Molecule to a Transmembrane Pore. Proceedings of the National Academy of Sciences of the United States of America 100(26):15498-503 (2003).
Gu, Li-qun, et al., Interaction of the Noncovalent Molecular Adapter, Beta-cyclodextrin, With the *Staphylococcal* Alpha-hemolysin Pore. Biophysical journal 79(4):1967-75 (2000).
Gu, Li-qun, et al., Stochastic Sensing of Organic Analytes by a Pore-forming Protein Containing a Molecular Adapter. Nature 398:686-690(1999).
Guimaraes, Carla P, et al., Site-specific C-terminal and internal loop labeling of proteins using sortase-mediated reactions. Nature Protocols 8(9):1787-1799 (2013).
Hammerstein, Anne, et al., Subunit Dimers of Alpha-hemolysin Expand the Engineering Toolbox for Protein Nanopores. The Journal of Biological Chemistry 286(16):14324-34 (2011).
Hardy, Simon. P, et al., CytK Toxin of Bacillus Cereus Forms Pores in Planar Lipid Bilayers and is Cytotoxic to Intestinal Epithelia. FEMS Microbiology Letters 197:47-51 (2001).
Hartmann, et al., Low temperature incommensurately modulated and noncollinear spin structure in FeCr2S4. Journal of Physics: Condensed Matter, vol. 22, 5:1-21 (2010).
Henning-Knechtel; Anja et al.: DNA-assisted oligomerization of pore-forming toxin monomers into precisely-controlled protein channels. Nucleic Acids Research 45(21):12057-12068 (2017).
Heron, Andrew, et al., Simultaneous Measurement of Ionic Current and Fluorescence from Single Protein Pores. Journal of the American Chemical Society 131(5):1652-1653 (2009).
Hille, Bertil, Ion Channels of Excitable Membranes, Third edition. Sinauer Associates Inc 37 Pages (2001).
Ho, Ching-Wen., et al., Engineering a nanopore with co-chaperonin function. Sci Adv 1(11):1-9 (2015).
Horton, Robert, et al. Engineering hybrid genes without the use of restriction enzymes: gene splicing by overlap extension. Gene 77(1):61-68 (1989).
Huang, Gang, et al., Detection of Single Amino Acid Differences in Haemoglobin From Blood Samples Using A Nanopore. ChemRxiv: 24 Pages (2021).
Huang, Gang, et al., Electro-Osmotic Capture And Ionic Discrimination of Peptide and Protein Biomarkers With Frac Nanopores. Nature Communications 8(935): 11 Pages (2017).
Huang, Gang, et al., Electro-Osmotic Vortices Promote the Capture of Folded Proteins by PlyAB Nanopores. Nano Letters 20(5):3819-3827 (2020).
Huang, Gang et al., FraC nanopores with adjustable diameter identify the mass of opposite-charge peptides with 44 dalton resolution. Nature Communications 10:1-10 (2019).
Huang, Gang, et al., PlyAB Nanopores Detect Single Amino Acid Differences in Folded Haemoglobin From Blood. Angewandte Chemie International Edition 61(34): 8 Pages (2022).
Huang, Kevin: Engineering biological nanopores for proteomics study. University of Groningen (2019). DOI: 10.33612/diss.102598418.
Huang, Rui, et al., Unfolding the mechanism of the AAA+ unfoldase VAT by a combined cryo-EM, solution NMR study. Proceedings of the National Academy of Sciences of the United States of America 1-10 (2016).
Huang, Shuo, et al., High-Throughput Optical Sensing of Nucleic Acids in a Nanopore Array. Nature Nanotechnology 10:986-991 (2015).
Huber, Eva, et al., A Unified Mechanism for Proteolysis and Autocatalytic Activation in the 20s Proteasome. Nature communications 7:1-10 (2016).
Huber, Eva, et al., The mammalian proteasome activator PA28 forms an asymmetric α4β3 complex. Structure 25(10):1473-1480 (2017).
Humbard, Matthew A, et al., Ubiquitin-like Small Archaeal Modifier Proteins (SAMPs) in Haloferax Volcanii. Nature 463:54-60 (2010).
Ivanov, Aleksandar P, et al., DNA tunneling detector embedded in a nanopore. Nano Letters 11(1):279-285 (2011).
Jiang, Jiansen, et al., Atomic structure of anthrax protective antigen pore elucidates toxin translocation. Nature 521(7553):545-549 (2015).
Kasianowicz, J J, et al., Characterization of individual polynucleotide molecules using a membrane channel. Proceedings of the National Academy of Sciences of the United States of America 93(24):13770-13773 (1996).
Kavalchuk, Mikhail, et al., Structural Basis of Prokaryotic Ubiquitin-like Protein Engagement and Translocation by the Mycobacterial Mpa-proteasome Complex. Nature Communications 13(1):276 (2022).
Kennedy, Eamonn., et al., Reading the primary structure of a protein with 0.07 nm3 resolution using a subnanometre-diameter pore. Nat Nanotechnol 11(11):968-976 (2016).
Kim, Yong-In, et al., Dynamics of Substrate Denaturation and Translocation by the Clpxp Degradation Machine. Molecular cell 5(4):639-648 (2000).
Kisselev, Alexei, et al., Why Does Threonine, and Not Serine, Function as the Active Site Nucleophile in Proteasomes ?. The Journal of Biological Chemistry 275(20):14831-14837 (2000).
Kowalczyk, Stefan W, et al., Detection of Local Protein Structures Along DNA Using Solid-state Nanopores. Nano Letters 10(1):324-328 (2010).
Krasilnikov, Oleg V, et al., Single Polymer Molecules in a Protein Nanopore in the Limit of a Strong Polymer-Pore Attraction. Physical Review Letters 97(1): 4 Pages (2006).
Kravats, Andrea, et al., Unfolding and translocation pathway of substrate protein controlled by structure in repetitive allosteric cycles of the ClpY ATPase. Proceedings of the National Academy of Sciences of the United States of America 108(6):2234-2239 (2011).
Krishnan R, Smrithi, et al., Autonomously Assembled Synthetic Transmembrane Peptide Pore. Journal of the American Chemical Society 141(7):2949-2959 (2019).
Krishnan Smrithi et al., Designed Alpha-helical Barrels for Charge-selective Peptide Translocation. Chemical Science 12(2):639-649 (2021).
Kristan, Katarina Crnigoj, et al., Molecular Mechanism of Pore Formation by Actinoporins. Toxicon 54(8):1125-34 (2009).
Kuehn et al., Proteasome activator PA28 and its interaction with 20 S proteasomes. Archives of biochemistry and biophysics 329(1):87-96 (1996).
Lamichhane, Usha, et al., Peptide translocation through the mesoscopic channel: binding kinetics at the single molecule level. Eur Biophys J 42(5):363-369 (2013).

(56) References Cited

OTHER PUBLICATIONS

Langklotz, Sina, et al., Structure and Function of the Bacterial AAA Protease FtsH. Biochim Biophys Acta 1823(1):40-48 (2012).

Laszlo, Andrew H, et al., Decoding long nanopore sequencing reads of natural DNA. Nature Biotechnology 32(8):829-833 (2014).

Li, Bisheng, et al., Black Phosphorus, a Rising Star 2D Nanomaterial in the Post-Graphene Era: Synthesis, Properties, Modifications, and Photocatalysis Applications. Small 15:1-30 (2019).

Li, et al., Detection of Peptides with Different Charges and Lengths by Using the Aerolysin Nanopore.4, 1-5 (2018).

Li, Jianfeng, et al., A comparative study of point-to-point algorithms for matching spectra. Chemometrics and Intelligent Laboratory Systems 82(1-2): 50-58 (2006).

Lide, David R, et al., CRC Handbook of Chemistry and Physics, 84th edition. Journal of the American Chemical Society 126(5):1585-1588 (2003).

Liu, Huanting, et al., An Efficient One-step Site-directed Deletion, Insertion, Single and Multiple-site Plasmid Mutagenesis Protocol. BMC biotechnology 8:91 (2008).

Liu, Wenxing et al., Probing Protein Nanopores With Poly Ethylene Glycols. Proteomics. vol. 22, No. 5-6 (2022): 16 pages.

Liu, Xi, et al., High Expression of Nfat2 Contributes to Carboplatin Resistance in Lung Cancer. Experimental and Molecular Pathology 110:104290 (2019).

Lowe, Jan, et al., Crystal structure of the 20S Proteasome From the archaeon T. acidophilum at 3.4 A resolution. Science 268(5210):533-539 (1995).

Lucas, Florian Leonardus Rudolfus, et al., The Manipulation of the Internal Hydrophobicity of FraC Nanopores Augments Peptide Capture and Recognition. ACS Nano 15(6):9600-9613 (2021).

Ma, Wenzhe, et al., Specificity of Trypsin and Chymotrypsin: Loop-motion-controlled Dynamic Correlation as a Determinantma. Biophysical journal 89 (2):1183-1193 (2005).

Macrander, Jason, et al., Evolution of the Cytolytic Pore-Forming Proteins (Actinoporins) in Sea Anemones. Toxins 8(12):1-16 (2016).

Maglia, Giovanni, et al., Analysis of Single Nucleic Acid Molecules With Protein Nanopores. Methods in Enzymology 475:591-623 (2010).

Maglia, Giovanni, et al., Enhanced translocation of single DNA molecules through alpha-hemolysin nanopores by manipulation of internal charge. Proceedings of the National Academy of Sciences of the United States of America 105(50):19720-19725 (2008).

Maillard, Rodrigo A, et al., ClpX(P) Generates Mechanical Force to Unfold and Translocate Its Protein Substrates. Cell 145(3):459-469 (2011).

Manning, Gerald S, The Persistence Length of DNA is Reached From the Persistence Length of Its Null Isomer Through an Internal Electrostatic Stretching Force. Biophysical Journal 91(10):3607-3616 (2006).

Manrao, Elizabeth A, et al., Nucleotide discrimination with DNA immobilized in the MspA nanopore. PLOS One 6(10): 7 Pages (2011).

Manrao, Elizabeth, et al., Reading DNA at Single-nucleotide Resolution With a Mutant MspA Nanopore and phi29 DNA Polymerase. Nature Biotechnology 30(4):349-353 (2012).

Martin, Andreas, et al., Pore Loops of the AAA+ ClpX Machine Grip Substrates to Drive Translocation and Unfolding. Nature Structural & Molecular Biology 15(11):1147-1151 (2008).

Martin, Andreas, et al., Rebuilt AAA + Motors Reveal Operating Principles for ATP-Fuelled Machines. Nature 437:1115-1120 (2005).

Mathe, Jerome, et al., Nanopore unzipping of individual DNA hairpin molecules. Biophysical Journal 87(5):3205-3212 (2004).

Mechaly et al.: Structural Insights into the Oligomerization and Architecture of Eukaryotic Membrane Pore-Forming Toxins. Structure 19:181-191 (2010). DOI 10.1016/j.str.2010.11.013.

Merstorf, Celine, et al., Wild Type, Mutant Protein Unfolding and Phase Transition Detected By Single-nanopore Recording. ACS Chemical Biology 7(4):652-658 (2012).

Mesa-Galloso, Haydee et al.: Disrupting a key hydrophobic pair in the oligomerization interface of the actinoporins impairs their pore-forming activity. Protein Science 26:550-565 (2017). https://onlinelibrary.wiley.com/doi/full/10.1002/pro.3104.

Miethke, Marcus, et al., Involvement of Bacillus Subtilis ClpE in CtsR Degradation and Protein Quality Control. Journal of Bacteriology 188(13):4610-4619 (2006).

Miles, George, et al., Assembly of the Bi-component Leukocidin Pore Examined by Truncation Mutagenesis. The Journal of Biological Chemistry 281(4):2205-14 (2006).

Miles, George, et al., The *Staphylococcal* Leukocidin Bicomponent Toxin Forms Large Ionic Channels. Biochemistry 40(29):8514-8522 (2001).

Mishra, Ribhav, et al., Proteasome-mediated Proteostasis: Novel Medicinal and Pharmacological Strategies for Diseases. Medicinal Research Reviews 38(6):1916-1973 (2018).

Mitchell, Jonathan, et al., Sequence-Dependent Persistence Lengths of DNA. Journal of Chemical Theory and Computation 13(4):1539-1555 (2017).

Mohammad, Mohammad, et al., Controlling a single protein in a nanopore through electrostatic traps. 130(12):4081-4088 (2008).

Morante, Koldo, et al., A Pore-Forming Toxin Requires a Specific Residue for Its Activity in Membranes with Particular Physicochemical Properties. Journal of Biological Chemistry 290(17):10850-10861 (2015).

Morante, Koldo et al.: Functional characterization of Val60, a key residue involved in the membrane-oligomerization of fragaceatoxin C, an actinoporin from Actinia fragacea. FEBS Letters 589(15):1840-1846 (2015). https://doi.org/10.1016/j.febslet.2015.06.012.

Motone, Keisuke, et al., Herding Cats: Label-based Approaches in Protein Translocation Through Nanopore Sensors For Single-molecule Protein Sequence Analysis. iScience 24(9): 14 Pages (2021).

Motone, Keisuke et al., Multi-pass, Single-molecule Nanopore Reading of Long Protein Strands With Single-amino Acid Sensitivity. bioRxiv : The Preprint Server for Biology (2023): 47 pages.

Motone; Keisuke et al.: Not if but when nanopore protein sequencing meets single-cell proteomics. Nature Methods 20:336-338 (2023).

Movileanu, Liviu, et al., Interactions of peptides with a protein pore. Biophysical Journal 89(2):1030-1045 (2005).

Movileanu, Liviu, et al., Interrogating single proteins through nanopores: challenges and opportunities. Trends in Biotechnology 27(6):333-341 (2009).

Muccio, Giovanni Di, et al., Geometrically Induced Selectivity and Unidirectional Electroosmosis in Uncharged Nanopores. ACS Nano 16(6):8716-8728 (2022).

Mullner, Daniel, et al., fastcluster: Fast Hierarchical, Agglomerative Clustering Routines for R and Python. Journal of Statistical Software 53(9): 1-18 (2013).

Niitsu: Al et al.: Membrane-spanning α-helical barrels as tractable protein-design targets. Phil. Trans. R. Soc. B 372:20160213 (2016).

Nivala, Jeff, et al., Discrimination Among Protein Variants Using An Unfoldase-coupled Nanopore. ACS Nano 8(12):12365-12375 (2014).

Nivala, Jeff, et al., Unfoldase-mediated Protein Translocation Through An α-hemolysin Nanopore. Nature Biotechnology 31(3):247-250 (2013).

Noakes, Matthew, et al., Increasing the Accuracy of Nanopore DNA Sequencing Using a Time-varying Cross Membrane Voltage. Nature Biotechnology 37(6):651-656 (2019).

Nouwen, Nico, et al., Charged Amino Acids in a Preprotein Inhibit SecA-dependent Protein Translocation. Journal of Molecular Biology 386(4):1000-1010 (2009).

Nuijens, Timo, et al., Engineering a Diverse Ligase Toolbox for Peptide Segment Condensation. Advanced Synthesis and catalysis 358: 9 Pages (2016).

Olivare, Adrian, et al., Mechanistic insights into bacterial AAA+ proteases and protein-remodelling machines. Nature reviews. Microbiology, vol. 14(1):33-44(2016).

Ortega, Joaquin, et al., Visualization of Substrate Binding and Translocation by the Atp-dependent Protease, ClpXp, Molecular cell 6(6):1515-1521 (2000).

Oukhaled, Abdel., et al., Transport of long neutral polymers in the semidilute regime through a protein nanopore. Phys Rev Lett 108(8):1-4 (2012).

(56) References Cited

OTHER PUBLICATIONS

Oukhaled, G, et al., Unfolding of Proteins and Long Transient Conformations Detected by Single Nanopore Recording. Physical review letters 98(15):158101 (2007).
Pastoriza-Gallego, Manuela, et al., Evidence of Unfolded Protein Translocation through a Protein Nanopore. ACS Nano 8(11):11350-11360 (2014).
Pavlenok, Mikhail, et al., Control of Subunit Stoichiometry in Single-chain MspA Nanopores. Biophysical Journal 121(5):742-754 (2022).
PCT/NL2017/050331 International Search Report and Written Opinion dated Sep. 5, 2017.
PCT/NL2019/050588 International Search Report and Written opinion dated Dec. 17, 2019 (Pub. No. WO2020055246).
PCT/NL2019/050588 International Search Report dated Dec. 17, 2019.
PCT/NL2020/050726 International Search Report and Written Opinion dated Feb. 19. 2021.
PCT/NL2022/050266 International Search Report dated Nov. 28, 2022.
PCT/NL2023/050568 International Search Report dated Jan. 24, 2024.
Piguet, Fabien, et al., Identification of single amino acid differences in uniformly charged homopolymeric peptides with aerolysin nanopore. Nature communications 9(966):1-13 (2018).
Purnell, Robert F, et al., Discrimination of single base substitutions in a DNA strand immobilized in a biological nanopore. ACS Nano 3(9):2533-2538 (2009).
Qiao Dan et al., Synthetic Macrocycle Nanopore for Potassium-Selective Transmembrane Transport. Journal of the American Chemical Society 143(39):15975-15983 (2021).
Rincon-Restrepo, Marcela., et al., Controlled translocation of individual DNA molecules through protein nanopores with engineered molecular brakes. 11(2):746-750 (2011).
Ripstein, Zev, et al., Structure of a AAA+ unfoldase in the process of unfolding substrate. eLife 6:e25754 (2017).
Robertson, Joseph WF, et al., Nanopore Sensing: a Physical-chemical Approach. Biochimica Et Biophysica Acta. Biomembranes 1863 (9):1-15 ( 2021).
Robertson, Joseph W F, et al., Single-molecule mass spectrometry in solution using a solitary nanopore. Proceedings of the National Academy of Sciences of the United States of America 104(20):8207-8211 (2007).
Rodriguez-Vazquez, Nuria, et al., Membrane-targeted Self-assembling Cyclic Peptide Nanotubes. Current Topics in Medicinal Chemistry 14(23):2647-61 (2014).
Rojko, Nejc et al.: Pore Formation by Actinoporins, Cytolysins From Sea Anemones. Biochimica et Biophysica Acta 1858(3):446-456 (2016).
Ros, Uris, et al., Differences in Activity of Actinoporins Are Related With the Hydrophobicity of Their N-Terminus. Biochimie 116:70-78 (2015).
Rosen, Christian B, et al., Single-molecule Site-specific Detection of Protein Phosphorylation With a Nanopore. Nature Biotechnology 32(2):179-181 (2014).
Rosen, Christian B, et al., Targeting the N Terminus for Site-selective Protein Modification. Nature Chemical Biology 13(7):697-705 (2017).
Sauciuc Adina et al., An Engineered Electroosmotic Flow Transports Unravelled Proteins Across Nanopores. bioRxiv (2023).
Sauciuc, Adina et al., Translocation of Linearized Full-length Proteins Through an Engineered Nanopore Under Opposing Electrophoretic Force. Nature Biotechnology (2023): 63 pages.
Sauer, Rolf, et al., Preoperative Versus Postoperative Chemoradiotherapy For Rectal Cancer. The New England Journal of Medicine. 351(17):1731-1740 (2004).
Schmidt, Bernhard, Hydrophilic Polymers. Polymers (Basel) 11(4): 693 (2019).
Schon, Peter, et al., Equinatoxin II Permeabilizing Activity Depends on the Presence of Sphingomyelin and Lipid Phase Coexistence. Biophysical Journal 95(2):691-698 (2008).
Scott, Alistair, et al., Constructing Ion Channels From Water-soluble A-helical Barrels. Nature chemistry 13(7):643-650 (2021).
Seemüller, Erika, et al., Proteasome From Thermoplasma Acidophilum: A Threonine Protease. Science 268(5210):579-82 (1995).
Serek-Heuberger, Justyna, et al., Two Unique Membrane-bound Aaa Proteins From Sulfolobus Solfataricus. Biochemical Society Transactions 37(1):118-122 (2009).
Shimizu, Keisuke, et al., De Novo Design of a Nanopore for Single-molecule Detection That Incorporates a β-hairpin Peptide. Nature Nanotechnology 17(1):67-75 (2022).
Shuang, Li et al.: Detection of peptides with different charge and length by aerolysin nanopore. ChemElectroChem 6(1):126-129 (2018. https://doi.org/10.1002/celc.201800288.
Singh, Satyendra, et al., Functional Domains of the ClpA and ClpX Molecular Chaperones Identified by Limited Proteolysis and Deletion Analysis. The Journal of Biological Chemistry 276(31):29420-29429 (2001).
Soskine, Misha, et al., Single-molecule Analyte Recognition With Clya Nanopores Equipped With Internal Protein Adaptors. Journal of the American Chemical Society 137(17):5793-5797 (2015).
Soskine, Misha, et al., Tuning the size and properties of ClyA nanopores assisted by directed evolution. Journal of the American Chemical Society 135(36):13456-13463 (2013).
Spaan, András, et al., Leukocidins: *Staphylococcal* bi-component pore-forming toxins find their receptors. Nature reviews. Microbiology 15(7):435-447 (2019).
Spruijt, Evan, et al., DNA scaffolds support stable and uniform peptide nanopores. Nature Nanotechnology 13:739-745 (2018).
Stadtmueller, Beth M et al.: Proteasome Activators. Molecular Cell 41:8-19 (2011).
Stefureac, Radu, et al., Nanopore Analysis of a Small 86-residue Protein. Small 4(1):59-63 (2008).
Stefureac, Radu, et al., Transport of Alpha-helical Peptides Through Alpha-hemolysin and Aerolysin Pores. Biochemistry 45(30):9172-9 (2006).
Stoddart, David., et al., DNA stretching and optimization of nucleobase recognition in enzymatic nanopore sequencing Nanotechnology 26(8):10-16 (2015).
Stoddart, David, et al., Functional Truncated Membrane Pores. Proceedings of the National Academy of Sciences of the United States of America 111(7):2425-2430 (2014).
Stoddart, David, et al., Multiple base-recognition sites in a biological nanopore: two heads are better than one. Angewandte Chemie International Edition English 49(3):556-559 (2010).
Stoddart, David, et al., Nucleobase recognition in ssDNA at the central constriction of the alpha-hemolysin pore. Nano Letters 10(9):3633-3637 (2010).
Stoddart, David, et al., Single-nucleotide discrimination in immobilized DNA oligonucleotides with a biological nanopore. Proceedings of the National Academy of Sciences of the United States of America 106(19):7702-7707 (2009).
Stranges, Benjamin, et al., Design and Characterization of a Nanopore-coupled Polymerase for Single-molecule Dna Sequencing by Synthesis on an Electrode Array. Proceedings of the National Academy of Sciences of the United States of America 113(44):E6749-E6756 (2016).
Stryer: Biochemistry 4th Ed. WH Freeman, New York. p. 18-23 (1995).
Sugiyama, Masaaki, et al., Spatial Arrangement and Functional Role of a Subunits of Proteasome Activator Pa28 in Hetero-oligomeric Form. Biochemical and biophysical research communications 432:141-145 (2013).
Suzuki, Carolyn K, et al., Functional Mechanics of the ATP-dependent Lon Protease—Lessons From Endogenous Protein and Synthetic Peptide Substrates. Biochimica Et Biophysica Acta 1784(5):727-35 (2008).
Talaga, David S, et al., Single-molecule Protein Unfolding in Solid State Nanopores. Journal of the American Chemical Society 131(26):9287-9297 (2009).

(56) References Cited

OTHER PUBLICATIONS

Tanaka, Koji, et al., Bidirectional Transformation of a Metamorphic Protein between the Water-Soluble and Transmembrane Native States. Biochemistry 54(46):6863-6866 (2015).
Tanaka, Koji et al.: Structural Basis For Self-assembly of a Cytolytic Pore Lined By Protein and Lipid. Nature Communications 6: 6337 (2015).
Thapa, Parashar, et al., Native chemical ligation: a boon to peptide chemistry. Molecules 19(9): 14461-83 (2014).
Too, Priscilla Hiu-mei, et al., Slippery Substrates Impair Function of a Bacterial Protease ATPase by Unbalancing Translocation Versus Exit. The Journal of Biological Chemistry 288(19):13243-57 (2013).
Toplak, Ana, et al., Peptiligase an Enzyme for efficient Chemoenzymatic peptide Synthesis and Cyclization in Water. Advanced Synthesis and catalysis 358:2140-2147 (2016).
Tsutsui, Makusu, et al., Sparse Multi-nanopore Osmotic Power Generators. Cell Press Physical Science 3:1-12 (2022).
UniProt XP 002796191, Review, 2009.
U.S. Appl. No. 16/317,119 Office Action dated Apr. 28, 2021.
Van Der Verren, Sander E, et al., A Dual-constriction Biological Nanopore Resolves Homonucleotide Sequences With High Fidelity. Nature biotechnology 38:1415-1420 (2020).
Versloot, Roderick Corstiaan Abraham, et al., β-Barrel Nanopores with an Acidic-Aromatic Sensing Region Identify Proteinogenic Peptides at Low pH. ACS Nano 16(5):7258-7268 (2022).
Vorobieva, Anastassia A, De Novo Design of Transmembrane ß Barrels. Science 371(6531): 1-25 (2021).
Waalace; Emma V.B. et al.: Identification of epigenetic DNA modifications with a protein nanopore. Chem. Commun. 46:8195-8197 (2010).
Wang, Jimin, et al., The structure of ClpP at 2.3 A resolution suggests a model for ATP-dependent proteolysis. Cell 91(4):447-456 (1997).
Wanunu, Meni, et al., DNA translocation governed by interactions with solid-state nanopores. Biophys J 95(10):4716-4725 (2008).
Wanunu, Meni., et al., Electrostatic focusing of unlabelled DNA into nanoscale pores using a salt gradient. Nat Nanotechnol 5(2):160-165 (2010).
Watanabe, Hirokazu, et al., Analysis of Pore Formation and Protein Translocation Using Large Biological Nanopores. Analytical Chemistry 89(21):11269-11277 (2017).
Wei, Bryan, et al., Complex Shapes Self-assembled From Single-stranded DNA tiles. Nature 485(7400):623-626 (2012).
Wendell, David, et al., Translocation of double-stranded DNA through membrane-adapted phi29 motor protein nanopores. Nature Nanotechnology 4(11):765-72 (2009).
Wilson, Jason S. et al.: Identification and structural analysis of the tripartite α-pore forming toxin of Aeromonas hydrophila. Nature Communications 10:2900 (2019).
Wloka, Carsten, et al., Alpha-Helical Fragaceatoxin C Nanopore Engineered for Double-Stranded and Single-Stranded Nucleic Acid Analysis. Angewandte Chemie 55(40):12494-12498 (2016).
Wong, C T A, et al., Polymer Capture by Electro-osmotic Flow of Oppositely Charged Nanopores. The Journal of chemical physics 126(16):164903 (2007).
Xue, Liang, et al., Solid-state Nanopore Sensors. Nature Reviews Materials 21 Pages (2020).
Ye, Cheng, et al., Pandemic-scale Phylogenetics. bioRxiv : the preprint server for biology 1-16 (2021).
Ying, Yi-Lun, et al., Handling a Protein With a Nanopore Machine. Nature Chemistry 13:1160-1162 (2021).
Yu, Luning et al.: Unidirectional Single-File Transport of Full-Length Proteins Through a Nanopore. Nature Biotechnology 41:1130-1139 (2023).
Yusupov, Marat, et al., Crystal Structure of the Ribosome at 5.5 a Resolution. Science 292(5518):883-896 (2001).
Zang, Shengli, et al., Bottom-up fabrication of a multi-component nanopore sensor that unfolds, processes and recognizes single proteins. BioRxiv 2020.
Zhang, Shengli, et al., Bottom-up Fabrication of a Proteasome-nanopore That Unravels and Processes Single Proteins. Nature Chemistry 13(12):1192-1199 (2021).
Zhao, Qitao, et al., Study of Peptide Transport Through Engineered Protein Channels. The Journal of Physical Chemistry B 133 (11):3572-3578 (2009).
Zhao, Yanan, et al., Single Molecule Spectroscopy of Amino Acids and Peptides by Recognition Tunneling. Nature Nanotechnology 9(6):466-473 (2014).
Zhao, Yingqi, et al., Label-Free Optical Analysis of Biomolecules in Solid-State Nanopores: Toward Single-Molecule Protein Sequencing. ACS Photonics 9:730-742 (2022).
Ziemski, Michal, et al., Cdc48-Like Protein of Actinobacteria (Cpa) is a Novel Proteasome Interactor in Mycobacteria and Related Organisms. Elife 29(7):e34055 (2018).

\* cited by examiner

|  | pH 7.5 | | | pH 4.5 | | |
|---|---|---|---|---|---|---|
|  | Conductance | | | Conductance | | |
|  | (nS) | S.D. | n | (nS) | S.D. | n |
| WT-FraC | | | | | | |
| Type I | 2.26 | 0.08 | 92 | 2.12 | 0.07 | 72 |
| Type II | 1.26 | 0.08 | 52 | 1.06 | 0.07 | 81 |
| Type III | / | / | / | 0.42 | 0.03 | 6 |
| W116S-FraC | | | | | | |
| Type I | 2.14 | 0.09 | 101 | 2.07 | 0.1 | 57 |
| Type II | 1.24 | 0.06 | 53 | 1.08 | 0.09 | 92 |
| Type III | / | / | / | 0.41 | 0.03 | 53 |
| W112S-W116S-FraC | | | | | | |
| Type I | 2.19 | 0.08 | 39 | 1.96 | 0.09 | 24 |
| Type II | 1.23 | 0.06 | 56 | 1.03 | 0.1 | 43 |
| Type III | / | / | / | 0.38 | 0.03 | 43 |
| D109S-FraC | | | | | | |
| Type I | 2.22 | 0.11 | 48 | 2.09 | 0.09 | 50 |
| Type II | 1.25 | 0.07 | 48 | 1.04 | 0.07 | 78 |
| Type III | 0.41 | 0.04 | 2 | 0.41 | 0.02 | 12 |
| D109S-W116S-FraC | | | | | | |
| Type I | 2.11 | 0.14 | 28 | 1.99 | 0.12 | 20 |
| Type II | 1.24 | 0.04 | 69 | 0.99 | 0.10 | 73 |
| Type III | 0.41 | 0.01 | 4 | 0.40 | 0.02 | 19 |

FIG. 2A

(i)

(ii)

(iii)

(iv)

| Peptide sequence | | M.W (g/mol) | Ires% (-50 mV) |
|---|---|---|---|
| Angio IV: | V Y I H P F | 774.4 | 1.1 ± 0.8 |
| Angio 4-8: | Y I H P F | 675.8 | 8.2 ± 0.4 |
| Endomorphin I: | Y P W F | 610.7 | 19.2 ± 0.5 |
| Leu-enkephalin: | Y G G F L | 555.6 | 34.5 ± 2.4 |

D10C W116S oxidized:

D10C W116S without oxidization:

SEQUENCE LISTING

```
<160> NUMBER OF SEQ ID NOS: 26

<210> SEQ ID NO 1
<211> LENGTH: 179
<212> TYPE: PRT
<213> ORGANISM: Actinia fragacea

<400> SEQUENCE: 1

Ser Ala Asp Val Ala Gly Ala Val Ile Asp Gly Ala Gly Leu Gly Phe
1               5                   10                  15

Asp Val Leu Lys Thr Val Leu Glu Ala Leu Gly Asn Val Lys Arg Lys
                20                  25                  30

Ile Ala Val Gly Ile Asp Asn Glu Ser Gly Lys Thr Trp Thr Ala Met
            35                  40                  45

Asn Thr Tyr Phe Arg Ser Gly Thr Ser Asp Ile Val Leu Pro His Lys
        50                  55                  60

Val Ala His Gly Lys Ala Leu Leu Tyr Asn Gly Gln Lys Asn Arg Gly
65                  70                  75                  80

Pro Val Ala Thr Gly Val Val Gly Val Ile Ala Tyr Ser Met Ser Asp
                85                  90                  95

Gly Asn Thr Leu Ala Val Leu Phe Ser Val Pro Tyr Asp Tyr Asn Trp
                100                 105                 110

Tyr Ser Asn Trp Trp Asn Val Arg Val Tyr Lys Gly Gln Lys Arg Ala
            115                 120                 125

Asp Gln Arg Met Tyr Glu Glu Leu Tyr Tyr His Arg Ser Pro Phe Arg
        130                 135                 140

Gly Asp Asn Gly Trp His Ser Arg Gly Leu Gly Tyr Gly Leu Lys Ser
145                 150                 155                 160

Arg Gly Phe Met Asn Ser Ser Gly His Ala Ile Leu Glu Ile His Val
                165                 170                 175

Thr Lys Ala

<210> SEQ ID NO 2
<211> LENGTH: 190
<212> TYPE: PRT
<213> ORGANISM: Artificial Sequence
<220> FEATURE:
<223> OTHER INFORMATION: 6xHis-WtFraC
```

<400> SEQUENCE: 2

```
Met Ala Ser Ala Asp Val Ala Gly Ala Val Ile Asp Gly Ala Gly Leu
1               5                   10                  15
Gly Phe Asp Val Leu Lys Thr Val Leu Glu Ala Leu Gly Asn Val Lys
                20                  25                  30
Arg Lys Ile Ala Val Gly Ile Asp Asn Glu Ser Gly Lys Thr Trp Thr
            35                  40                  45
Ala Met Asn Thr Tyr Phe Arg Ser Gly Thr Ser Asp Ile Val Leu Pro
50                  55                  60
His Lys Val Ala His Gly Lys Ala Leu Leu Tyr Asn Gly Gln Lys Asn
65                  70                  75                  80
Arg Gly Pro Val Ala Thr Gly Val Val Gly Val Ile Ala Tyr Ser Met
                85                  90                  95
Ser Asp Gly Asn Thr Leu Ala Val Leu Phe Ser Val Pro Tyr Asp Tyr
                100                 105                 110
Asn Trp Tyr Ser Asn Trp Trp Asn Val Arg Val Tyr Lys Gly Gln Lys
            115                 120                 125
Arg Ala Asp Gln Arg Met Tyr Glu Glu Leu Tyr Tyr His Arg Ser Pro
130                 135                 140
Phe Arg Gly Asp Asn Gly Trp His Ser Arg Gly Leu Gly Tyr Gly Leu
145                 150                 155                 160
Lys Ser Arg Gly Phe Met Asn Ser Ser Gly His Ala Ile Leu Glu Ile
                165                 170                 175
His Val Thr Lys Ala Gly Ser Ala His His His His His His
                180                 185                 190
```

<210> SEQ ID NO 3
<211> LENGTH: 580
<212> TYPE: DNA
<213> ORGANISM: Artificial Sequence
<220> FEATURE:
<223> OTHER INFORMATION: 6xHis-WtFraC

<400> SEQUENCE: 3

```
atggcgagcg ccgatgtcgc gggtgcggta atcgacggtg cgggtctggg ctttgacgta      60
ctgaaaaccg tgctggaggc cctgggcaac gttaaacgca aaattgcggt agggattgat     120
aacgaatcgg gcaagacctg gacagcgatg aataccctat tccgttctgg tacgagtgat     180
attgtgctcc cacataaggt ggcgcatggt aaggcgctgc tgtataacgg tcaaaaaaat     240
cgcggtcctg tcgcgaccgg cgtagtgggt gtgattgcct atagtatgtc tgatgggaac     300
acactggcgg tactgttctc cgtgccgtac gattataatt ggtatagcaa ttggtggaac     360
gtgcgtgtct acaaaggcca gaagcgtgcc gatcagcgca tgtacgagga gctgtactat     420
catcgctcgc cgtttcgcgg cgacaacggt tggcattccc ggggcttagg ttatggactc     480
aaaagtcgcg gctttatgaa tagttcgggc cacgcaatcc tggagattca cgttaccaaa     540
gcaggctctg cgcatcatca ccaccatcac tgataagctt                           580
```

<210> SEQ ID NO 4
<211> LENGTH: 20
<212> TYPE: DNA
<213> ORGANISM: Artificial Sequence
<220> FEATURE:
<223> OTHER INFORMATION: T7 promotor

<400> SEQUENCE: 4

```
taatacgact cactataggg                                                   20
```

```
<210> SEQ ID NO 5
<211> LENGTH: 19
<212> TYPE: DNA
<213> ORGANISM: Artificial Sequence
<220> FEATURE:
<223> OTHER INFORMATION: T7 terminator

<400> SEQUENCE: 5
gctagttatt gctcagcgg                                                 19

<210> SEQ ID NO 6
<211> LENGTH: 29
<212> TYPE: DNA
<213> ORGANISM: Artificial Sequence
<220> FEATURE:
<223> OTHER INFORMATION: W112S Forward primer

<400> SEQUENCE: 6
acgattataa tagctatagc aattggtgg                                      29

<210> SEQ ID NO 7
<211> LENGTH: 26
<212> TYPE: DNA
<213> ORGANISM: Artificial Sequence
<220> FEATURE:
<223> OTHER INFORMATION: W116S Forward primer

<400> SEQUENCE: 7
attggtatag caatagctgg aacgtg                                         26

<210> SEQ ID NO 8
<211> LENGTH: 38
<212> TYPE: DNA
<213> ORGANISM: Artificial Sequence
<220> FEATURE:
<223> OTHER INFORMATION: W112116S Forward primer

<400> SEQUENCE: 8
gtacgattat aatagctata gcaatagctg gaacgtgc                            38

<210> SEQ ID NO 9
<211> LENGTH: 27
<212> TYPE: DNA
<213> ORGANISM: Artificial Sequence
<220> FEATURE:
<223> OTHER INFORMATION: D109S Reverse primer

<400> SEQUENCE: 9
tgctatacca attatagctg tacggca                                        27

<210> SEQ ID NO 10
<211> LENGTH: 21
<212> TYPE: PRT
<213> ORGANISM: Artificial Sequence
<220> FEATURE:
<223> OTHER INFORMATION: Endothelin 2 peptide

<400> SEQUENCE: 10

Cys Ser Cys Ser Ser Trp Leu Asp Lys Glu Cys Val Tyr Phe Cys His
1               5                   10                  15

Leu Asp Ile Ile Trp
            20

<210> SEQ ID NO 11
```

```
<211> LENGTH: 21
<212> TYPE: PRT
<213> ORGANISM: Artificial Sequence
<220> FEATURE:
<223> OTHER INFORMATION: Endothelin 1 peptide

<400> SEQUENCE: 11

Cys Ser Cys Ser Ser Leu Met Asp Lys Glu Cys Val Tyr Phe Cys His
1               5                   10                  15

Leu Asp Ile Ile Trp
            20

<210> SEQ ID NO 12
<211> LENGTH: 17
<212> TYPE: PRT
<213> ORGANISM: Artificial Sequence
<220> FEATURE:
<223> OTHER INFORMATION: Dynorphin A peptide

<400> SEQUENCE: 12

Tyr Gly Gly Phe Leu Arg Arg Ile Arg Pro Lys Leu Lys Trp Asp Asn
1               5                   10                  15

Gln

<210> SEQ ID NO 13
<211> LENGTH: 14
<212> TYPE: PRT
<213> ORGANISM: Artificial Sequence
<220> FEATURE:
<223> OTHER INFORMATION: Pre angiotensinogen peptide

<400> SEQUENCE: 13

Asp Arg Val Tyr Ile His Pro Phe His Leu Val Ile His Asn
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Angiotensin I peptide

<400> SEQUENCE: 14

Asp Arg Val Tyr Ile His Pro Phe His Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: c-Myc 410-419 peptide

<400> SEQUENCE: 15

Glu Gln Lys Leu Ile Ser Glu Glu Asp Leu
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Angiotensin 1-9 peptide

<400> SEQUENCE: 16

Asp Arg Val Tyr Ile His Pro Phe His
```

```
1               5

<210> SEQ ID NO 17
<211> LENGTH: 8
<212> TYPE: PRT
<213> ORGANISM: Artificial Sequence
<220> FEATURE:
<223> OTHER INFORMATION: Angiotensin II peptide

<400> SEQUENCE: 17

Asp Arg Val Tyr Ile His Pro Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Asn1Val5 Angiotensin II peptide

<400> SEQUENCE: 18

Asn Arg Val Tyr Val His Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Angiotensin A peptide

<400> SEQUENCE: 19

Ala Arg Val Tyr Ile His Pro Phe
1               5

<210> SEQ ID NO 20
<211> LENGTH: 7
<212> TYPE: PRT
<213> ORGANISM: Artificial Sequence
<220> FEATURE:
<223> OTHER INFORMATION: Angiotensin III

<400> SEQUENCE: 20

Arg Val Tyr Ile His Pro Phe
1               5

<210> SEQ ID NO 21
<211> LENGTH: 7
<212> TYPE: PRT
<213> ORGANISM: Artificial Sequence
<220> FEATURE:
<223> OTHER INFORMATION: Ile7 Angiotensin III peptide

<400> SEQUENCE: 21

Arg Val Tyr Ile His Pro Ile
1               5

<210> SEQ ID NO 22
<211> LENGTH: 6
<212> TYPE: PRT
<213> ORGANISM: Artificial Sequence
<220> FEATURE:
<223> OTHER INFORMATION: Angiotensin IV peptide

<400> SEQUENCE: 22

Val Tyr Ile His Pro Phe
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: Angiotensin 4-8 peptide

<400> SEQUENCE: 23

Tyr Ile His Pro Phe
1               5

<210> SEQ ID NO 24
<211> LENGTH: 4
<212> TYPE: PRT
<213> ORGANISM: Artificial Sequence
<220> FEATURE:
<223> OTHER INFORMATION: Endomorphin I peptide

<400> SEQUENCE: 24

Tyr Pro Trp Phe
1

<210> SEQ ID NO 25
<211> LENGTH: 5
<212> TYPE: PRT
<213> ORGANISM: Artificial Sequence
<220> FEATURE:
<223> OTHER INFORMATION: Met5 Enkephalin peptide

<400> SEQUENCE: 25

Tyr Gly Gly Phe Met
1               5

<210> SEQ ID NO 26
<211> LENGTH: 5
<212> TYPE: PRT
<213> ORGANISM: Artificial Sequence
<220> FEATURE:
<223> OTHER INFORMATION: Leucine Enkephalin peptide

<400> SEQUENCE: 26

Tyr Gly Gly Phe Leu
1               5
```

BIOLOGICAL NANOPORES HAVING TUNABLE PORE DIAMETERS AND USES THEREOF AS ANALYTICAL TOOLS

CROSS-REFERENCE

This application is a National Stage Entry of International Patent Application No. PCT/NL2019/050588, filed Sep. 11, 2019, which claims the benefit of European Application No. 18193722.8, filed Sep. 11, 2018, each of which is entirely incorporated herein by reference.

SEQUENCE LISTING

The instant application contains a sequence listing which has been submitted electronically in ASCII format and is hereby incorporated by reference in its entirety. Said ASCII copy, created on Feb. 19, 2021, is named Sequence-Listing-as-filed-19feb.2021-20885-4501.txt, and is 9,181 bytes in size.

BACKGROUND

The invention relates generally to the field of nanopores and the use thereof in analyzing biopolymers and other (biological) compounds. In particular, it relates to engineered Fragaceatoxin C (FraC) nanopores and their application in single molecule analysis, such as single molecule peptide sequencing.

DETAILED DESCRIPTION

Biological nanopores are proteins that open nanoscale water conduits on biological or synthetic membranes. Under an external potential, the ionic current across single nanopore is used to recognize analytes traversing the nanopore. Most notably, nanopores are now used to sequence nucleic acids at the single-molecule level. In nanopore DNA sequencing, individual nucleic acid trains are threaded base-by-base through nanopores, while the ionic current is used to identify individual nucleobases[1,2].

Watanabe et al. (Analytical Chemistry 2017 89 (21), 11269-11277) describe the analysis of pore formation and detection of a single protein molecule using a large nanopore among five different pore-forming proteins, including FraC. It is demonstrated that the identification of appropriate pores for nanopore sensing can be achieved by classifying the channel current signals and performing noise analysis.

However, the sequencing of proteins with nanopores presents a new set of challenges. Amino acids have a larger chemically variability compared to nucleobases, and they cannot be uniformly captured or stretched by the electrical potential inside the nanopore. Furthermore, enzymes that process proteins or polypeptides amino acid-by-amino acid are not yet known.

Alternatively, proteins might be first fragmented and then the mass of individual peptides identified by nanopore currents. This approach would be similar to conventional protein sequencing approaches using tandem mass spectrometry. A nanopore peptide mass identifier, however, would have the advantage of being low-cost and portable and single-molecule. The latter is important because it would allow the analysis of the chemical heterogeneity in post-translational modifications and, especially when coupled to high-throughput devices, permit the detection of low-abundance proteins. Previous work with PEG molecules[3,4,5,6,7,8], neutral peptides[9] or oligosaccharides[10], uniformly charged peptides[11,12,13,14,15] and other peptides[16] revealed that there might be a direct correlation between the depth of the current blockade and the molecular weight of polymers, when the composition of the analyte is uniform. On the other hand, a wealth of other studies, including work with DNA[17,18] and amino acid enantiomers[19] revealed that the chemical identity of molecules and especially the charge inside the nanopore[20] have a strong and unpredictable effect on the ionic current, suggesting that the identification of the mass of complex biopolymers such as peptides might not be possible. An additional complication is that peptides of opposite charge are not efficiently captured and analysed at a fixed potential[16,21,22,23,24]. Finally, the diameter and geometry of biological nanopores cannot be easily adapted to study the array of sizes, shapes and chemical composition of polypeptides in solution.

Recently we have shown that octameric Fragaceatoxin C (FraC) nanopores[25] from the sea anemone *Actinia fragacea* can be used to study DNA[26], proteins and peptides[27]. See also WO2018/012963 in the name of the present applicant. The transmembrane region of FraC is unique compared to other nanopores used in biopolymer analysis as it is formed by α-helices that describe a sharp and narrow constriction at the trans exit of the nanopore. Crucially, we showed that an electro-osmotic flow across the nanopore can be engineered to capture polypeptides at a fixed potential despite their charge composition[27]. However, peptides smaller than 1.6 kDa in size translocated too fast across the nanopore to be sampled.

Based on these studies, the present inventors realized and recognized that nanopores with a smaller diameter are required to detect peptides with lower molecular weight. Therefore, they aimed at providing a strategy that allows for tuning the diameter of FraC nanopores, such that a larger range of peptides sizes can be identified.

It was surprisingly found that the FraC nanopore can be engineered to induce the formation of different nanopore types (herein referred to Type II and/or Type III) when comprised in the context of a lipid bilayer, thereby creating a biological nanopore with sub-nm constriction. Importantly, these novel, narrow types of nanopores allow for distinguishing (small) peptides differing by the substitution of one amino acid with a ~40 Da resolution, while previous nanopore studies only reported differences of about 200 Da. Moreover, at selected pH conditions the FraC nanopore signal directly correlated to the mass of the peptide. The invention herewith provides a new and unique approach for the single-molecule identification of proteins based on nanopores.

In one embodiment, the invention relates to a system comprising oligomeric Fragaceatoxin C (FraC) nanopores comprised in a lipid bilayer, wherein the sum of the nanopore fraction in the Type II state and the nanopore fraction in the Type III state represents at least 60% of the total number of FraC nanopores.

For example, the sum of the Type II and Type III state nanopores represents at least 65%, preferably at least 70%, of the total number of FraC nanopores.

As used herein, the term "Type II" state refers to nanopores having an apparent heptameric stoichiometry, and/or a conductance of about 1.22-1.26 nS when assayed at pH 7.5 in a 1M NaCl solution or about 0.99-1.08 nS when assayed at pH 4.5 in a 1 M KCl solution. Conductance values are suitably determined by collecting single channels under −50 mV applied potential using 1 M NaCl, 15 mM Tris pH 7.5, or 1 M KCl, 0.1 M citric acid, 180 mM Tris base pH 4.5.

Type II FraC nanopores are furthermore characterized by an apparent pore size (at the narrowest constriction) of about 1.1 nm as calculated from homology modeling.

As used herein, the term "Type III" state refers to nanopores having an apparent hexameric stoichiometry, and/or a conductance of about 0.37-0.43 nS when assayed at pH 4.5 in a 1M KCl solution.

Type III FraC nanopores are furthermore characterized by a pore size (at the narrowest constriction) of about 0.8 nm as shown by homology modeling.

Accordingly, in one embodiment, the invention provides a system comprising oligomeric FraC nanopores comprised in a lipid bilayer, wherein the sum of the nanopore fraction in the heptameric (Type II) state and the nanopore fraction in the hexameric (Type III) state represents at least 60% of the total number of FraC nanopores.

In another embodiment, the invention provides a system comprising oligomeric FraC nanopores comprised in a lipid bilayer, wherein the sum of (i) the nanopore fraction showing a conductance of about 0.99-1.08 nS (Type II) when assayed at pH 4.5 in a 1 M KCl solution and (ii) the nanopore fraction showing a conductance of about 0.37-0.43 nS (Type III) when assayed at pH 4.5 in a 1 M KCl solution represents at least 60% of the total number of FraC nanopores.

Still further, the invention provides a system comprising oligomeric FraC nanopores comprised in a lipid bilayer, wherein the sum of the nanopore fraction having an apparent pore size of about 1.1 nm (Type II) and the nanopore fraction having an apparent pore size of about 0.8 nM (Type III) represents at least 60% of the total number of FraC nanopores.

The relative amounts of Type II and Type III nanopores can vary according to needs. In one aspect, at least 40%, preferably at least 50%, of the FraC nanopores is in the Type II state. Alternatively, or additionally, at least 15%, preferably at least 20%, of the FraC nanopores is in the Type III state.

In one embodiment, at least 60%, preferably at least 70%, of the FraC nanopores is in the Type II state. In another embodiment, at least 60%, preferably at least 70%, of the FraC nanopores is in the Type III state.

Also encompassed are systems comprising essentially one oligomeric form/Type of FraC. For example, in one embodiment, at least 90%, preferably at least 95%, of the FraC nanopores is present in the Type II state. In a specific aspect, all of the FraC nanopores are in the Type II state. In another embodiment, at least 90%, preferably at least 95%, of the FraC nanopores is present in the Type III state. In a specific aspect, all of the FraC nanopores are in the Type III state. The different oligomeric forms of FraC can be readily isolated using liquid chromatographic techniques, including size-exclusion, affinity, reverse-phase or ion exchange chromatography.

In a specific aspect, the FraC nanopores comprise or consist of mutant FraC monomers comprising one or more mutations that weaken the interaction between the nanopore and the lipid bilayer, i.e. the lipid interface.

Very good results are obtained when FraC is mutated at position W112 and/or W116. For example, in one embodiment, FraC is mutated at position W112, preferably while W116 is not mutated, or at position W116, preferably while W112 is not mutated. In a further embodiment, the FraC mutant comprises a mutation at both positions W112 and W116. According to the present invention, the W residues are substituted with either S, T, A, N, Q or G, preferably with S or T. FraC contains 179 amino acids with relative molecular weight of 20 kDa. The cDNA for FraC is available under the accession number FM958450 in GenBank. The polypeptide sequence of FraC is available under the accession number B9W5G6 in UniProt (SEQ ID NO: 1).

Moreover, the crystal structure of FraC was resolved in 2010 and deposited in the RCSB PDB under the accession number 3LIM. In a mutant according to the invention, the residue numbering corresponds to the residue numbering as in the FraC sequence according to UniProtKB accession number B9W5G6 (SEQ ID NO: 1).

The importance of (conserved) tryptophan residues for the functioning of pore-forming toxins has been previously studied. Tanaka et al.[25] revealed structures of FraC corresponding to four different stages of its activation route, namely the water-soluble form, the lipid-bound form, an assembly intermediate and the transmembrane pore. Mutational analysis revealed that mutant W112R/W116F lacks the ability to bind to lipid membrane, thus becoming completely inactive. Garcia-Linares et al., 2016 studied the role of the tryptophan residues in the specific interaction of the sea anemone *Stichodactyla helianthus*'s Actinoporin Sticholysin II (StnI) with biological membranes.

It was found that residues W110 and W114 (corresponding to W112 and W116 of FraC) sustain the hydrophobic effect, which is one of the major driving forces for membrane binding in the presence of cholesterol. Notably, while the authors state that "the results obtained support actinoporins' Trp residues playing a major role in membrane recognition and binding", they also conclude that "their residues have an only minor influence on the diffusion and oligomerization steps needed to assemble a functional pore". Herewith, the findings of the present inventors that W112 and/or W116 are suitably engineered to tune the oligomeric state of FraC could not have reasonably been predicted in view of the prior art.

Hence, in one aspect the invention provides a system comprising oligomeric FraC nanopores comprised in a lipid bilayer, wherein the FraC nanopores comprise mutant FraC monomers comprising a mutation at position W112 and/or W116, preferably wherein the W residue(s) is/are independently substituted with either S, T, A, N, Q or G, preferably with S or T. In one embodiment, it comprises or consists of FraC mutant W112S or W112T. In another embodiment, it comprises or consists of mutant W116S or W116T. In a still further embodiment, the system comprises or consists of FraC mutant W112S/W116S, W112T/W116S or W112S/W116T.

The inventors noticed that type II FraC nanopores inserted in the lipid bilayer more efficiently at low pH. Therefore, to increase the production of type II nanopores at physiological pH, aspartic acid at position 109, which is located at the lipid interface, was exchanged for an uncharged residue. Satisfactorily, the fraction of type II nanopores at pH 7.5 increased from 23.0±4.9% to 48±3.6%, and a small fraction of type III nanopores appeared.

The invention also provides a system comprising oligomeric FraC nanopores comprised in a lipid bilayer, wherein the FraC nanopores comprise mutant FraC monomers comprising a mutation at position D109, preferably herein said mutation comprises the substitution of D with an uncharged residue, such as S or T, more preferably with S. The concomitant substitution of tryptophan at position 116 with serine showed a further small increased in the fraction of type I and type II nanopores at pH 7.5.

Therefore, the invention further relates to a system comprising oligomeric FraC nanopores comprised in a lipid bilayer, wherein the FraC nanopores comprise mutant FraC monomers comprising mutation D109S and one or both of W112S and W116S.

A system with the nanopores of the invention can accommodate peptides ranging from 22 to 4 amino acids in length. Even smaller peptides can be detected using further fine-tuning of the transmembrane region of the nanopore, for example by introducing amino acids with bulky side-chains. We also showed that the nanopores can discriminate differences between an alanine and glutamate (~40 Da) in mixture of peptides. Furthermore, the inventors found that at exactly pH 3.8 the ionic signal of the peptides depended on the mass the analyte, while at higher pH values the current signal of negatively charged peptides was higher than expected from their mass alone.

Without wishing to be bound by any theory, the inventors' explanation is that the peptides analyzed lost their charge, while the constriction of the nanopore still retained enough negative charge to recognize the peptide charge. Most likely, a negatively charged constriction is important for creating an electrophoretic environment for peptide-mass recognition. At the same time, the electrostatic interaction of the constriction with negatively charged analytes might prevent the correct position of the analyte within the reading frame of the nanopore.

Presumably, peptides need to be uniformly charged which can be achieved by lowering the pH of the solution. At the same time, however, the constriction of the nanopore should be negatively charged in order to obtain optimal mass recognition. Obtaining both effects may be challenging, because by lowering the pH the charge of the constriction also becomes less charged.

Therefore, in addition to the amino acid substitution(s) disclosed herein above, mutant FraC monomers may comprise one or more unnatural amino acids comprising a moiety that holds a negative charge at low pH, preferably wherein said moiety is a sulfate or phosphate group. In one embodiment, a reside (e.g. at position 10) is mutated to cysteine and then oxidized, hence introducing a sulfonic (or sulfinic) group at that position. The charge of such group remains negative over the all pH range. With this approach, the recognition of peptides could be improved. Alternatively, peptides might be chemically modified (e.g. by esterification) to neutralize the negative charge.

In a system according to the invention, the FraC nanopores are comprised in a lipid bilayer. The reconstitution of FraC nanopores in lipid bilayers has been described in the art. Typically, the lipid bilayer comprises phosphatidylcholine (PC), preferably 1,2-diphytanoyl-sn-glycero-3-phosphocholine (DPhPC), optionally in combination with sphingomyelin (SM). Very good results are obtained when DPhPC and SM are present in about equal amounts by mass.

When a system according to the invention is in use, the nanopore is typically positioned between a first liquid medium and a second liquid medium, wherein at least one liquid medium comprises an analyte, and wherein the system is operative to detect a property of the analyte. In one embodiment, the system is operative to detect a property of the analyte comprises subjecting the nanopore to an electric field such that the analyte electrophoretically and/or electroosmotically translocates through the nanopore. As exemplified herein below, a system provided herein is particularly suitable for the analysis of a proteinaceous substance, preferably a peptide, more preferably a peptide up to about 30 amino acids in length. More in particular, a system of the invention provides for capture of peptides with different charge, recognition of the mass of the peptide and a resolution up to only 40 Da.

However, this is in no way to be understood that the invention is limited to applications relating to peptide analysis. For example, other analytes that can be detected using a system of the invention include (non-proteinaceous) biomarkers, antibiotics or other drugs, DNA, metabolites and small biological molecules.

The invention further relates to a mutant Fragaceatoxin C (FraC) polypeptide comprising one or more of the above mutations. These polypeptides are advantageously used in an (analytical) system herein disclosed. Also provided is an isolated nucleic acid molecule encoding a mutant FraC polypeptide according to the invention, and an expression vector comprising the isolated nucleic acid molecule. Still further, the invention provides a host cell comprising said expression vector.

In one embodiment, the mutant FraC polypeptide comprises a mutation at position D109, W112 and/or W116. For example, it comprises a mutation at W112 (optionally while W116 is not mutated) or it comprises a mutation at W116 (optionally while W112 is not mutated). In one embodiment, it comprises a mutation at both W112 and W116. As indicated herein above, the mutation(s) may comprise the substitution of D or W with S, T, A, N, Q or G, preferably with S or T. In a specific aspect, the invention provides mutant FraC W112S, FraC W116S, or FraC W112S/W116S, or its encoding nucleic acid molecule, or vector comprising the same. Still further, it provides a polypeptide comprising mutation D109S, preferably wherein the mutant is D109S/W116S, or its encoding nucleic acid molecule, or vector comprising the same.

Any one of these mutations may be supplemented with one or more unnatural amino acids comprising a moiety that holds a negative charge at low pH, for example wherein said moiety is a sulfate, sulfonic acid or phosphate group. Preferred positions for introducing such negative charge residue(s) include one or more of positions 10, 17 and 24.

In a specific aspect, the mutation W116 is supplemented with mutation D10C. The thiol group of the cysteine is then oxidized to sulfonic acid e.g. by incubation of FraC double mutant monomers with 10% (v/v) hydrogen peroxide. It was found that the introduction of a sulfonic acid moiety at position 10 of FraC gives rise to oligomerised pores that show a quiet signal in electrophysiology recordings as compared to a more noisy signal observed for nanopores that had not been subjected to oxidation. Accordingly, in one embodiment the invention provides a mutant comprising the D10C substitution, preferably in combination with one or more of W112S, W116S and D109S, more preferably in combination with at least W116S.

A further embodiment relates to a method for providing a system according to the invention, comprising the steps of
  providing recombinant FraC monomers;
  contacting said monomers with liposomes to assemble them into oligomers;
  recovering the oligomers from the liposomes; and
  contacting the oligomers with a lipid bilayer, which may contain sphingomyelin, to allow the formation of FraC nanopores.

In one embodiment, the contacting with a lipid bilayer is performed at a pH below 4.5, preferably below 4.0.

A method of the invention may furthermore comprise the step of isolating a fraction comprising FraC nanopores in the Type II state, and/or a fraction comprising FraC nanopores in the Type III state. In one aspect, it comprises isolating different oligomeric forms of FraC using a liquid chromatographic technique, including size-exclusion, affinity, reverse-phase or ion exchange chromatography.

A peptide mass-detecting FraC nanopore system of the present invention is advantageously integrated in real-time protein sequencing system. To that end, the system preferably comprises one or more further modifications.

In one embodiment, a protease-unfoldase pair is attached directly above (i.e. on the cis side of) the FraC nanopore. Then, cleaved peptides will be sequentially recognized and translocated across the nanopore. For example, the barrel-shaped ATP-dependent ClpXP protease is an ideal candidate because it can encase the digested peptides preventing its release in solution. Another approach is based on a protein complex that constitutes the proteasome, or any other protease. For example, the complex includes the 20S alpha/beta subunits of the proteasome, and the 19S regulatory particle, of which the ATPase is the minimal required unit. However, other proteases could also be used. The protease will cleave the polypeptide specifically (for example it could cut after a positively charged residue or a negatively charged residue or a aromatic residue etcetera), or it will be engineered to cut specifically, or it will cut at nonspecific locations within the polypeptide chain. The protease will ideally encase the substrate and will allow the docking of other components (e.g. unfoldases) to feed the polypeptide to the unfoldase active site.

The attachment may be of a covalent or non-covalent nature. For example, it can achieved by chemical attachment, by genetic fusion, or by introducing a binding loop into the FraC nanopore that can interact non-covalently with the peptidase.

We demonstrated that the peptides entering the cis side of the nanopore have a high probability of exiting the nanopore to the trans chamber, which will prevent duplicate detection events. Furthermore, we showed that at low pH peptides are likely to be captured and their mass recognized by the nanopore at a fixed applied potential irrespectively of their chemical composition. If such low pH values will not be compatible with enzymatic activity, asymmetric solutions on both side of the nanopore can be used[34,35]. In such system, conditions in the cis side can be tuned to optimize the ATPase activity of the unfoldase-peptidase, while the pH and ionic strength of the trans side can be optimized to capture and recognize individual peptides.

A FraC nanopore or a mutant FraC polypeptide as provided herein is advantageously used in all sorts of analyte analysis, including peptide or DNA analysis, preferably wherein peptide analysis comprises peptide mass detection and/or peptide sequencing. However, whereas the advantageous properties of a system provided herein are demonstrated in the context of peptide analysis, a person skilled in the art will appreciate that it can be used for various applications. Other possible applications of the invention include the following:

Peptide post-modification detection (glycosylation etc), proteomics;
DNA sequencing with higher accuracy, or DNA post-modification detection (methylation etc);
Other small analytes detection or polymers analysis with higher resolution.
Single molecule protein and DNA sequencing;
Directly peptides, biomarkers, antibiotics and small molecules detection in human samples;
Trapping of different size proteins for binding ligands analysis like glucose etc.

Mass spectrometry is the workhorse of the proteomics field. At present, the nanopore system falls short from the resolution of commercial mass spectrometers. A peptide mass-analyzer device based on FraC nanopores as herein disclosed has distinctive advantages compared to conventional mass spectrometers, which are expensive, extremely complex and unwieldy, and are not single-molecule. By contrast, nanopores can be integrated in portable and low-cost devices containing hundreds of thousands of individual sensors. Hence, in one embodiment the FraC nanopore system is integrated in a portable device comprising a plurality of individual FraC nanopore systems as herein described.

In addition, the electrical nature of the signal allows sampling biological samples in real-time. Furthermore, since the nanopore reads individual molecules, the signal contains additional information not available for ensemble techniques. In particular, single-molecule detection, especially when coupled to high throughput analysis, will allow detecting low abundance peptides and to unravel the chemical heterogeneity in post translational modifications, challenges that are hard to address with conventional mass spectrometry. For example, the invention also provides for the use of a FraC nanopore system or a mutant FraC polypeptide in single molecule detection, preferably in combination with high throughput analysis.

LEGEND TO THE FIGURES

Figure 1B:
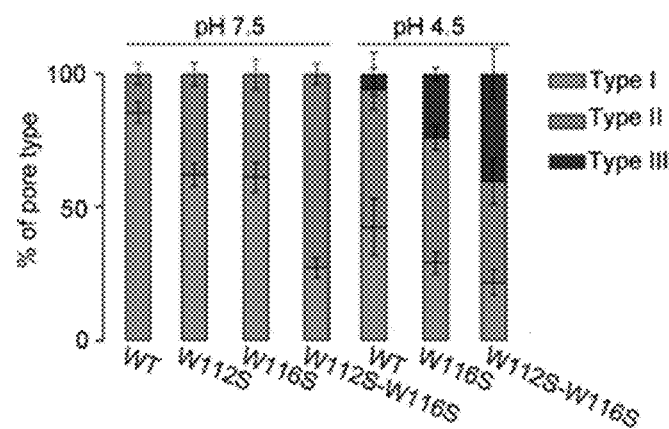
Figure 1C:
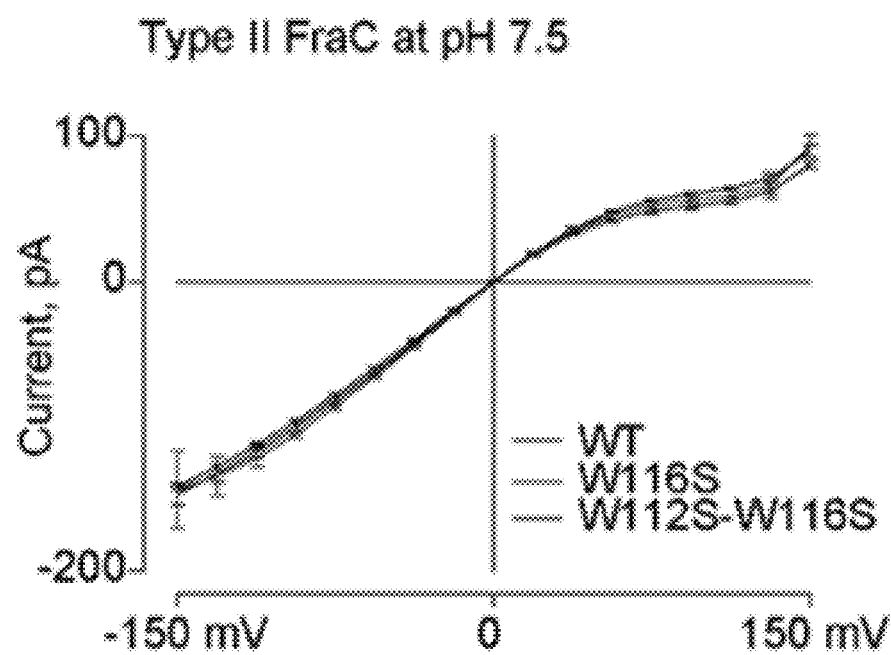
Figure 1D:
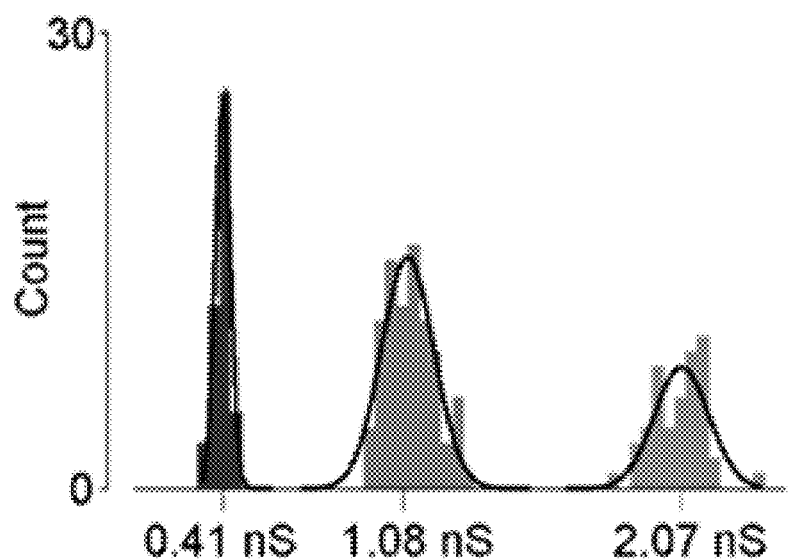
Figure 1E:
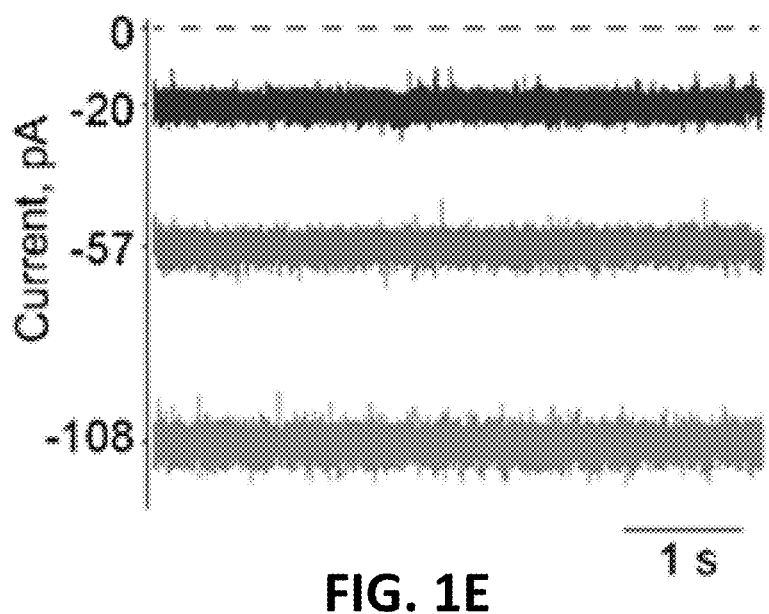
Figure 1F:
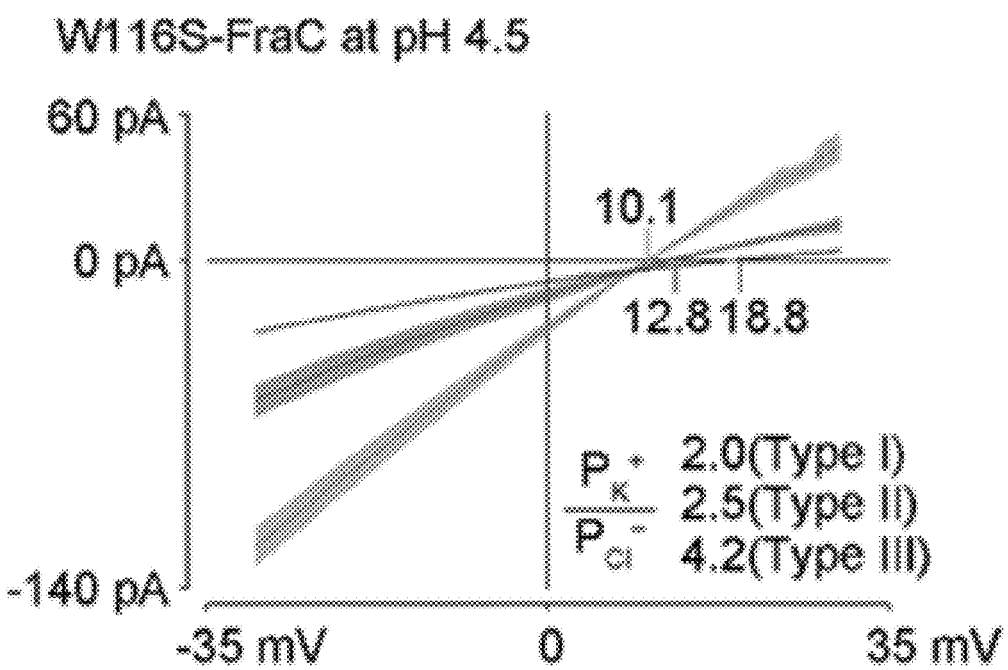
Figure 1G:
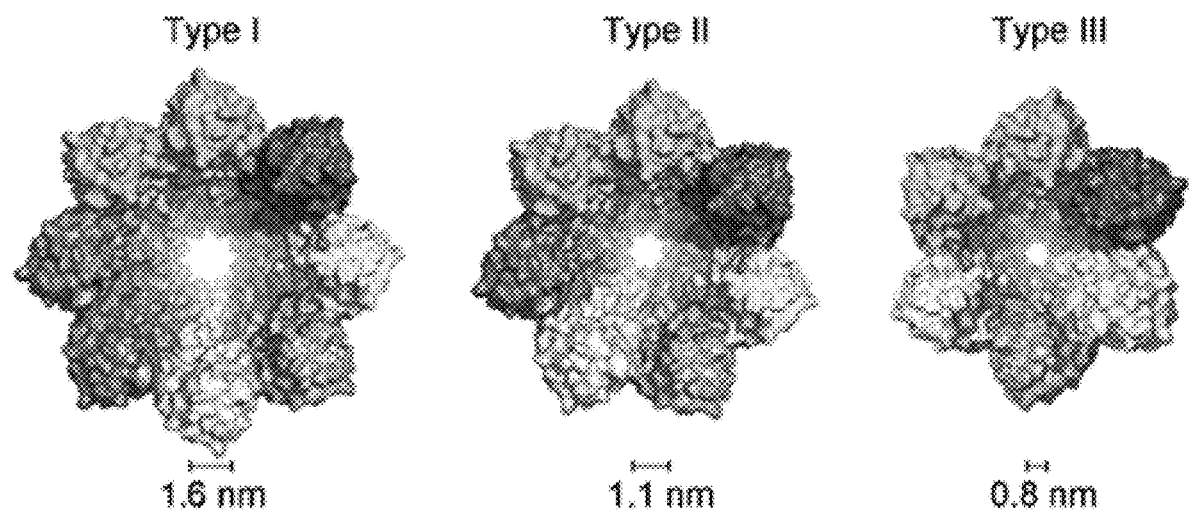

FIGS. 1A-1G. Preparation and characterization of type I, type II and type III FraC nanopores. FIG. 1A, Cut through of a surface representation of WT-FraC oligomer (PDB: 4TSY)[25] colored according to the vacuum electrostatic potential as calculated by Pymol. One protomer is shown as a carton presentation with tryptophans 112 and 116 displayed as spheres. FIG. 1B, Percentage of the distribution of type I, type II and type III for WT-FraC, W112S-FraC, W116S-FraC and W112S-W116S-FraC at pH 7.5 and 4.5. FIG. 1C, IV curves of type II nanopores formed by WT-FraC, W116S-FraC and W112S-W116S-FraC at pH 7.5 (15 mM Tris·HCl, 1 M KCl). FIG. 1D, Single nanopore conductance of W116S-FraC in 1 M KCl (0.1 M citric acid and 180 mM Tris base) at pH 4.5. FIG. 1E, Typical current traces for the three nanopore types of W116S-FraC in 1 M KCl at pH 4.5 under −50 mV applied potential. FIG. 1F, Reversal potentials measured under asymmetric condition of KCl (1960 mM cis, 467 mM trans) at pH 4.5 for the three W116S-FraC nanopore types. The ion selectivity was given by using the Goldman-Hodgkin-Katz equation (equation 1). FIG. 1G, Molecular models of the three type FraC nanopores constructed from the FraC crystals structure using the symmetrical docking function of Rosetta. The electrophysiology recordings were performed with 10 kHz sampling and 2 kHz filter. The error bars and color shadow in the I-V curves are standard deviations from three repeats at least.

Figure 2B:
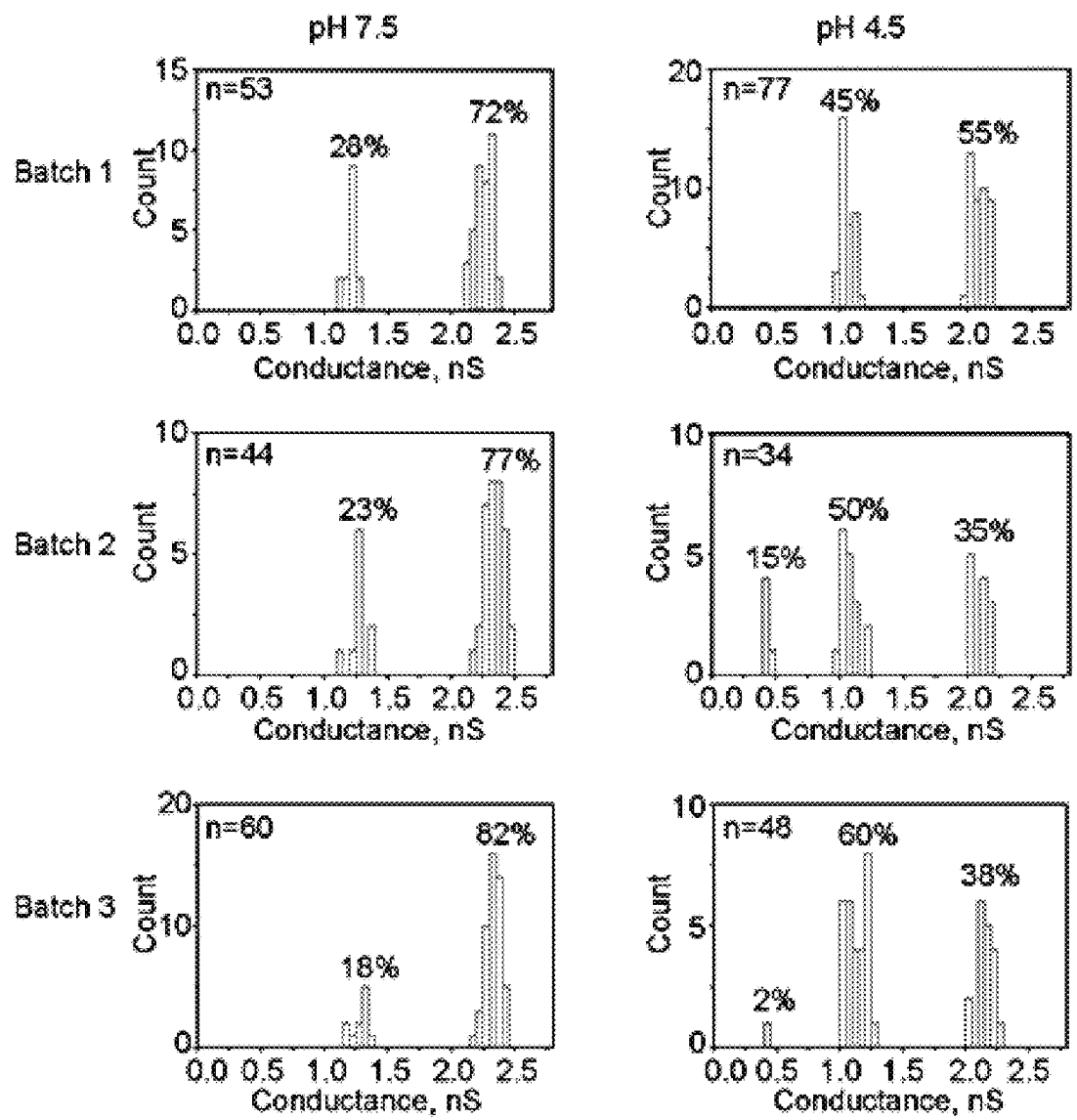
Figure 2C:
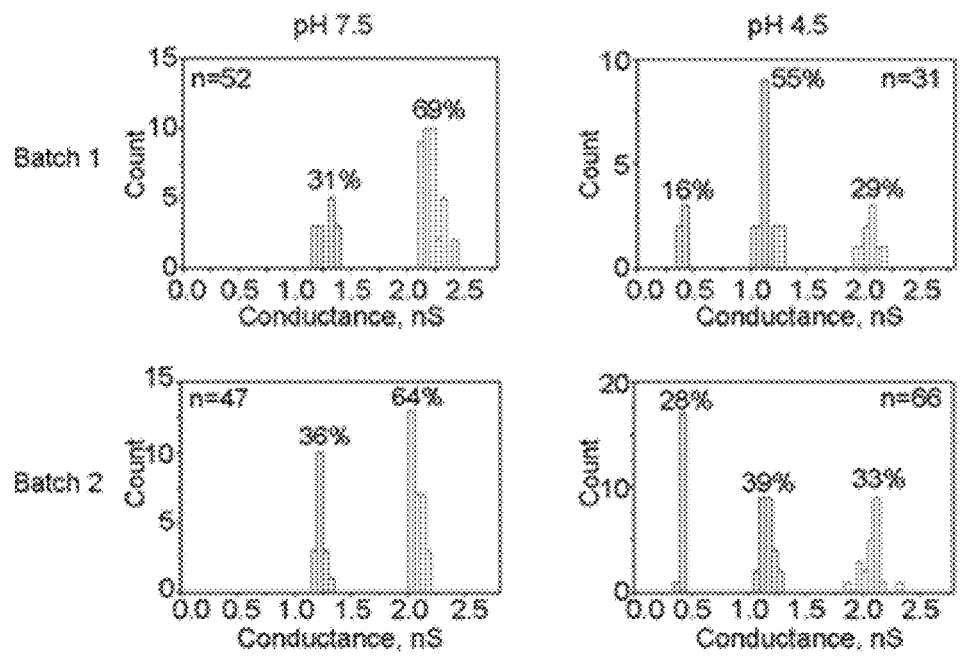
Figure 2D:
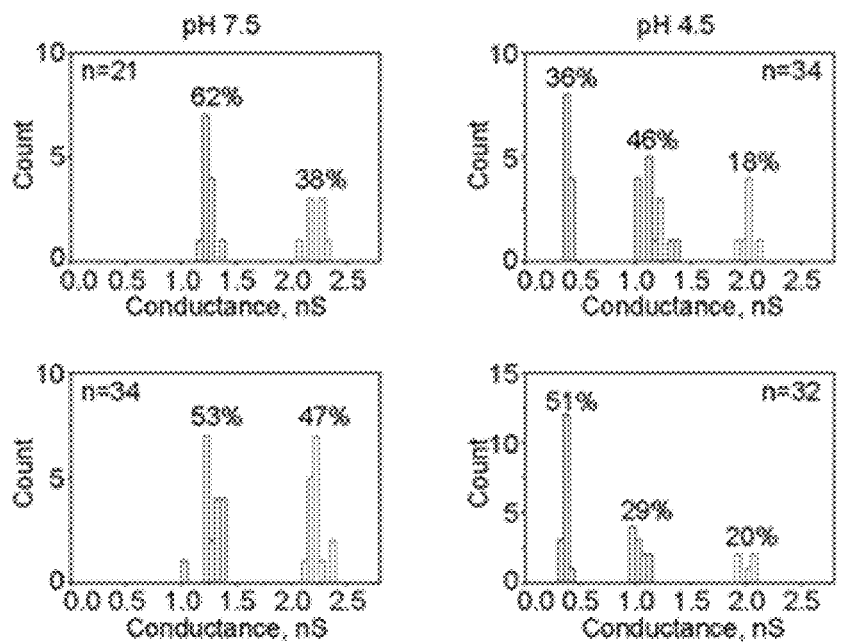
Figure 2E:
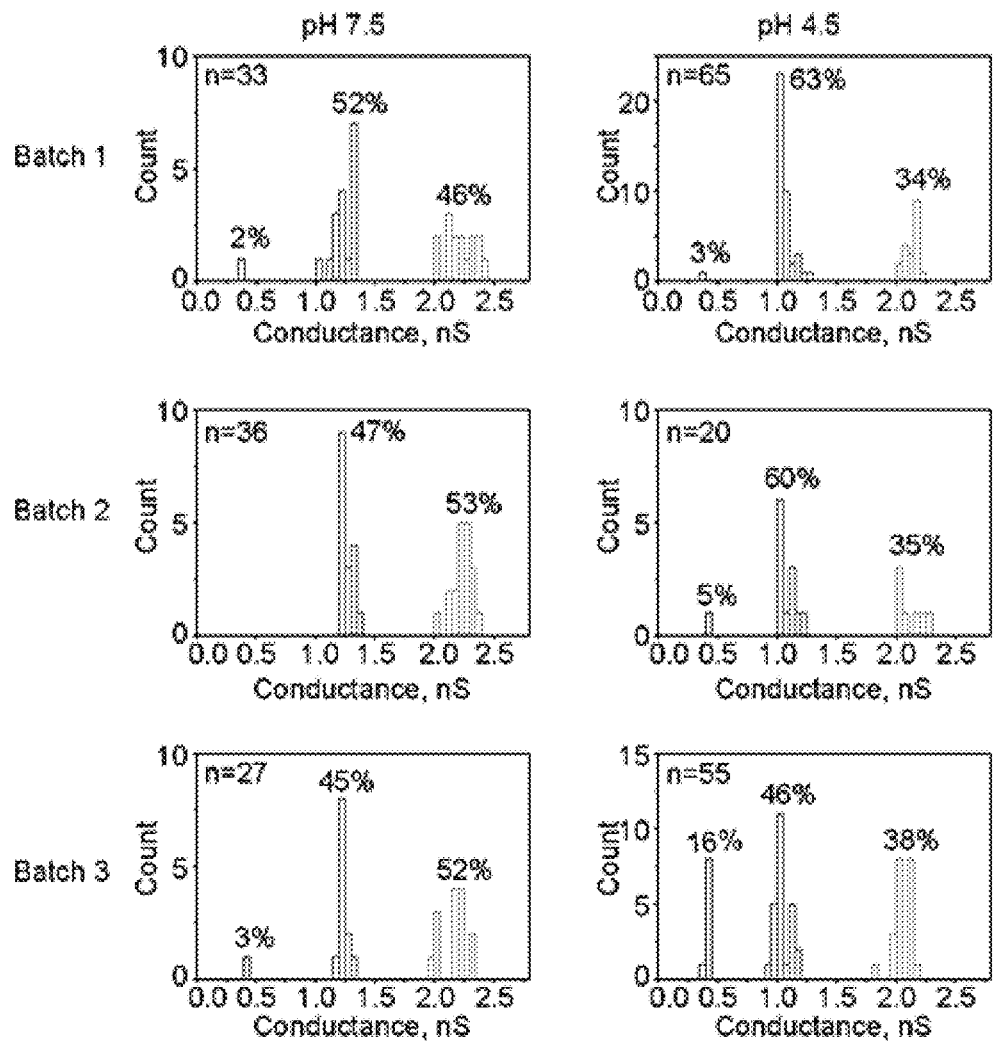
Figure 2F:
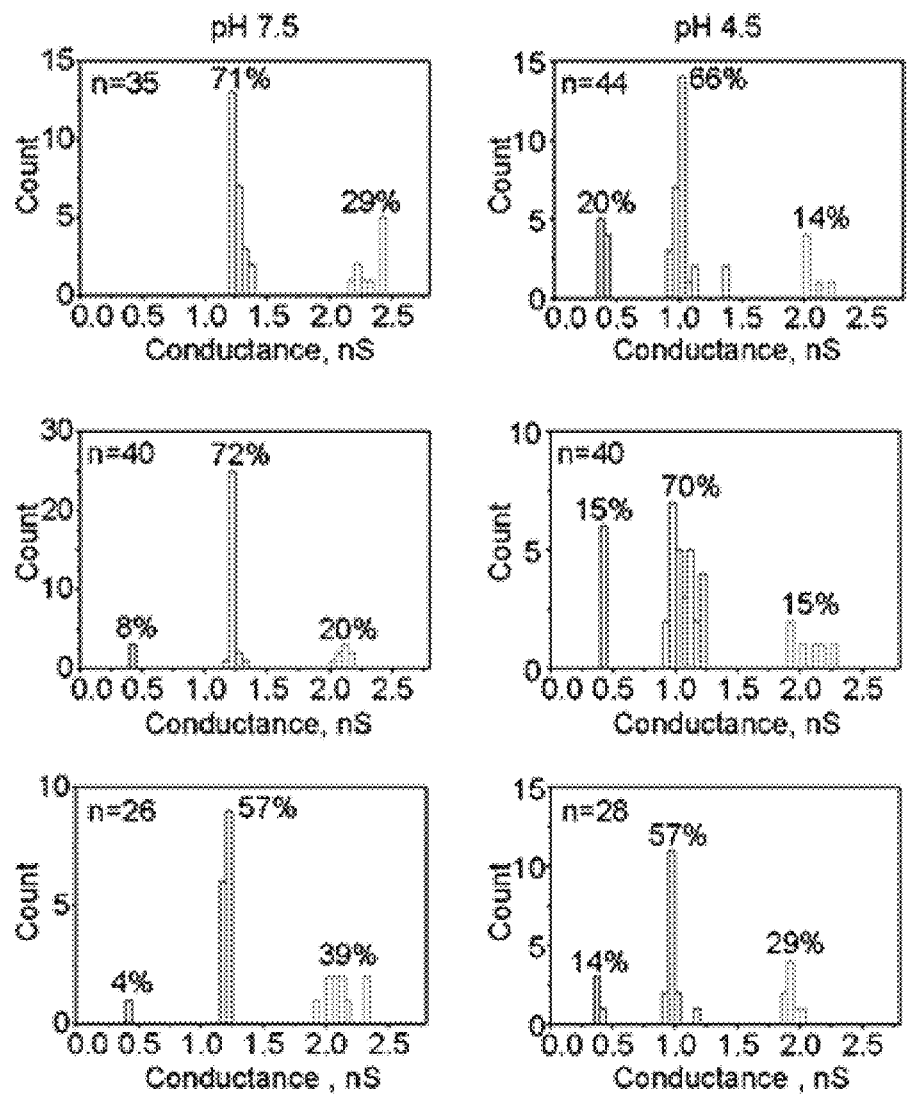

FIGS. 2A-2F. Single channel conductance distributions of FraC nanopores at pH 7.5 and 4.5. FIG. 2A, The table reports the average conductance values which were obtained by fitting Gaussian functions to conductance histograms. S.D. represents the standard deviation of all single channels (number given as n). FIGS. 2B-2F, Each panel represents a different batch of FraC nanopores as indicated. Single channels were collected under −50 mV applied potential. pH 7.5 and 4.5 were obtained using 1 M NaCl, 15 mM Tris, or 1 M KCl, 0.1 M citric acid, 180 mM Tris base respectively.

Figure 3A:
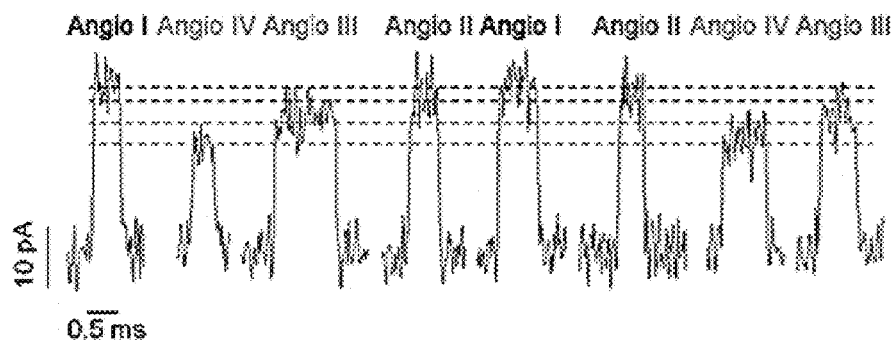
Figure 3A:
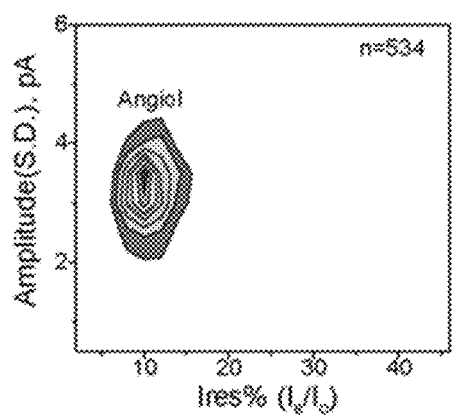
Figure 3A:
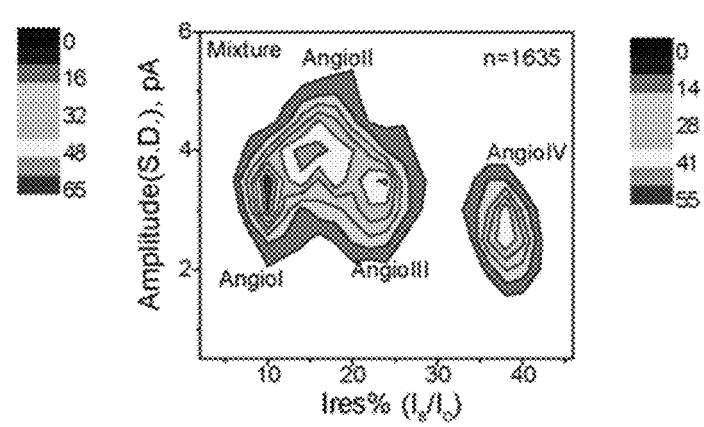
Figure 3B:
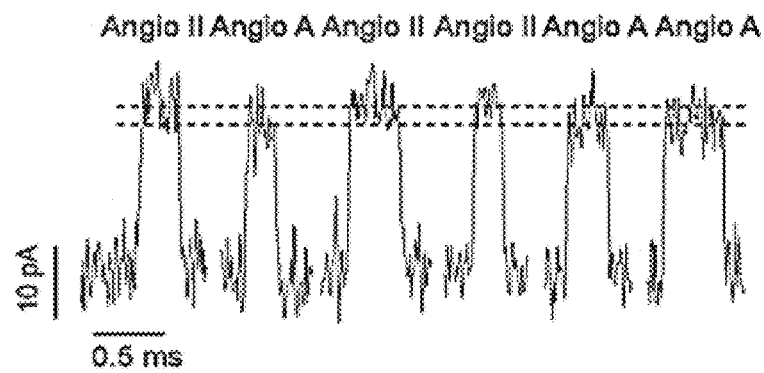
Figure 3B:
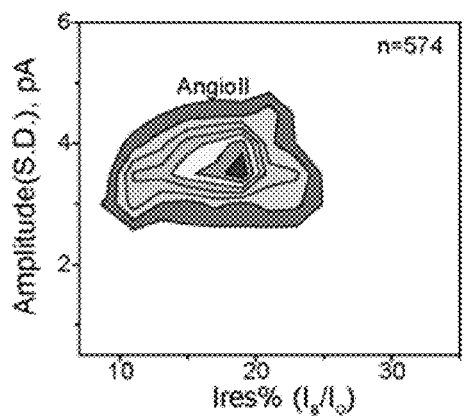
Figure 3B:
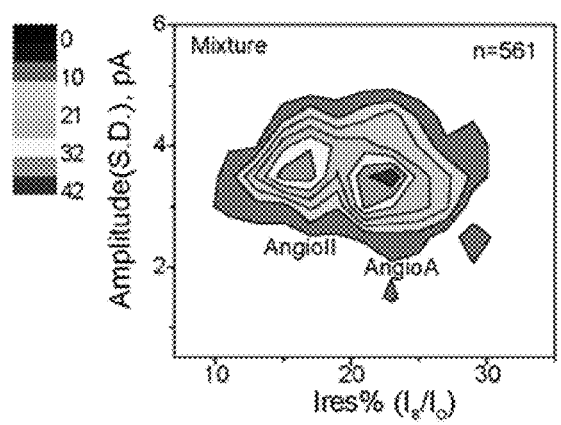

FIGS. 3A-3B. Discrimination of angiotensin peptides in mixture with type II W116S-FraC nanopores. FIG. 3A, (i)

Sequences of angiotensin I, II, III and IV with corresponding Ires % measured at −30 mV. (ii) Typical blockades provoked by the four angiotensin peptides. (iii) Color density plot of the Ires % versus the standard deviation of the current amplitude for angiotensin I added to the cis compartment, and after the further addition of angiotensin II, angiotensin III, and angiotensin IV to the cis chamber (iv). FIG. 3B, Discrimination of angiotensin II and angiotensin A. (i) Table showing the sequences, the molecular weights and the Ires % of the peptides. The peptides differ by one amino acid as shown in red. (ii) Representative traces of the peptide blockades. Color density plot of the Ires % versus the standard deviation of the current amplitude for angiotensin II blockades prior (iii) and after (iv) the further addition of angiotensin A to the cis chamber. All measurements and recordings were performed in pH 4.5 buffer containing 1 M KCl, 0.1 M citric acid, 180 mM Tris base with a 50 kHz sampling and 10 kHz filter. Standard deviations were calculated from minimum three repeats. Color density plot was created with Origin. FIG. 3A discloses SEQ ID NOS 14, 17, 20, and 22, respectively, in order of appearance. FIG. 3B discloses SEQ ID NOS 17 and 19, respectively, in order of appearance.

Figure 4A:
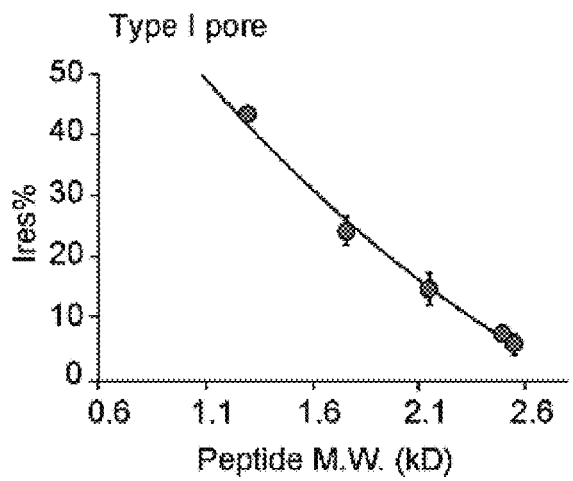
Figure 4B:
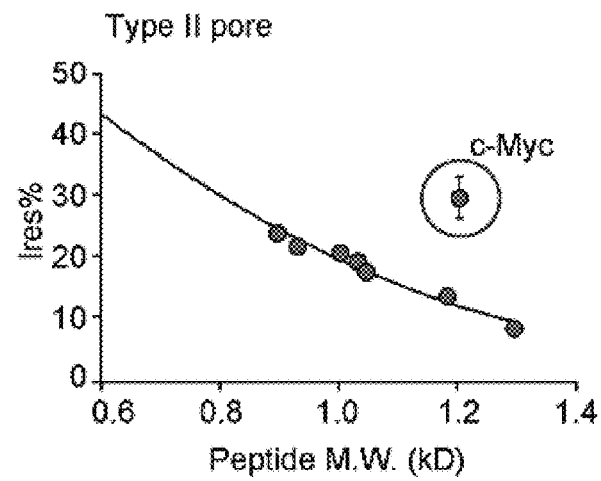
Figure 4C:
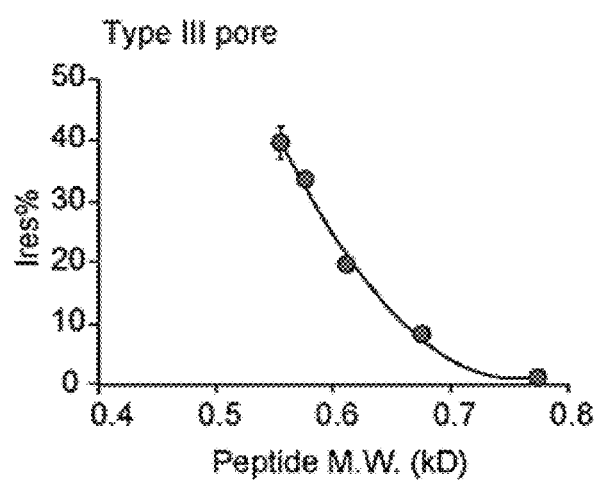

FIGS. 4A-4C. Evaluation of biological peptides having different chemical compositions. Relation between the molecular weight and Ires % of peptide using: (FIG. 4A) type I WT-FraC nanopores, (FIG. 4B) type II W116S-FraC nanopores and (FIG. 4C) type III W112S-W116S-FraC nanopores at pH 4.5. The solid line represents a second order polynomial fitting. Current blockades were measured at −30 mV for type I and II pore, and at −50 mV for type III pore. Error bars are standard deviations obtained from at least three measurements.

Figures 5A, 5B:
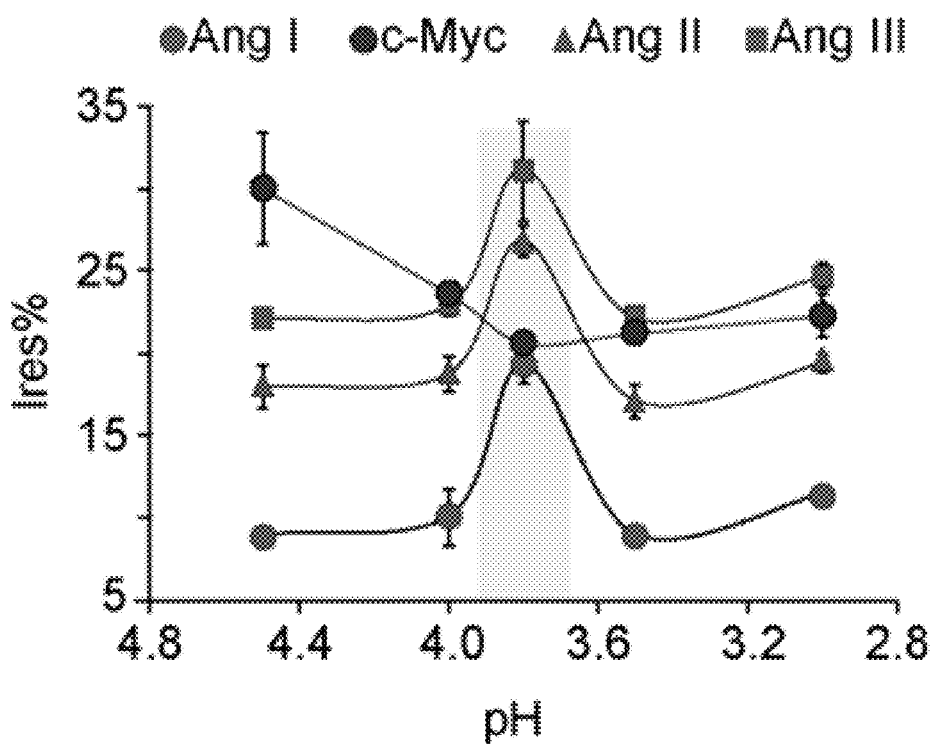
Figure 5C:
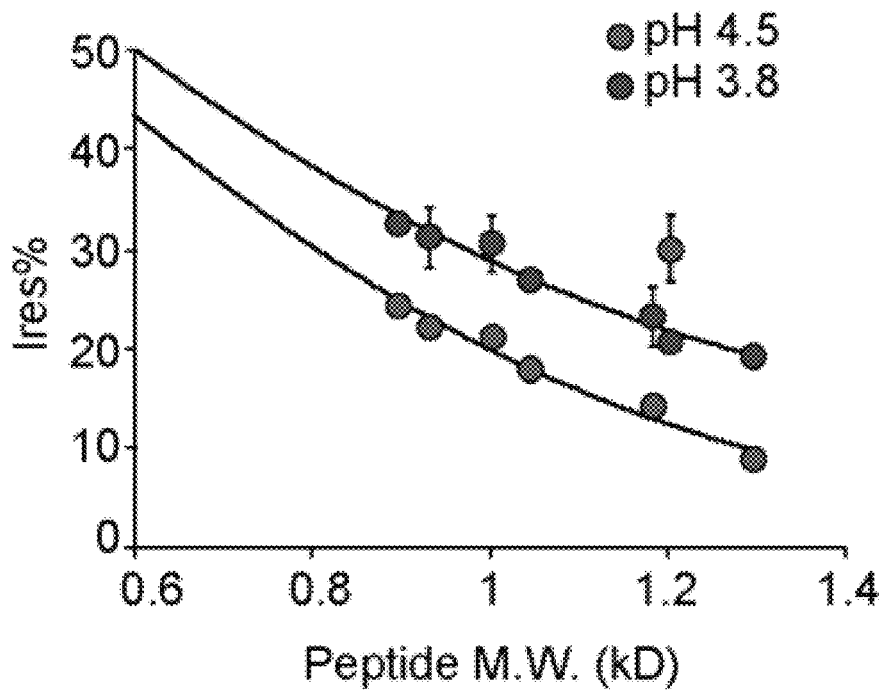
Figure 5D:
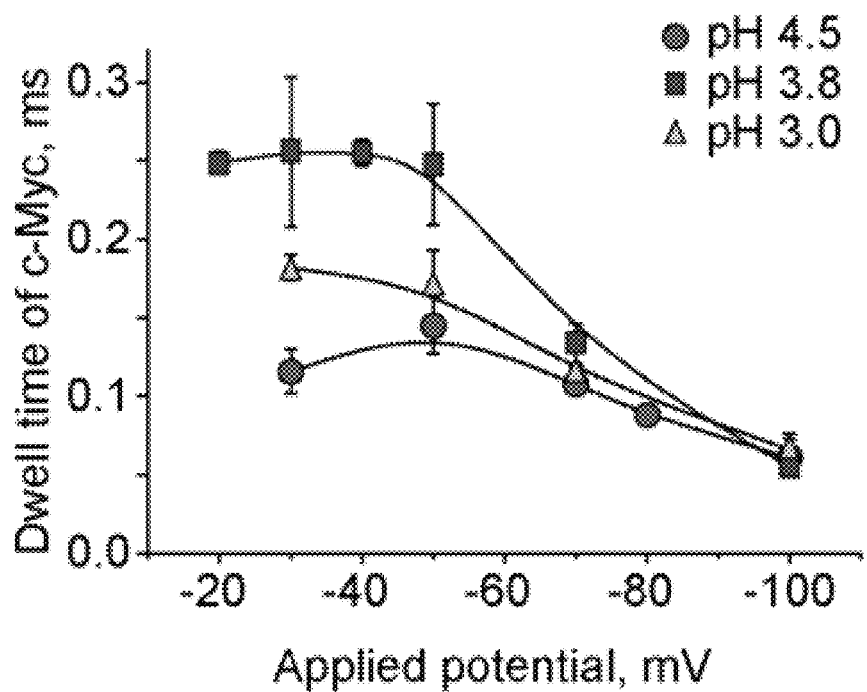

FIGS. 5A-5D. A nanopore peptide mass spectrometer at pH 3.8. FIG. 5A, Amino acid sequences of four different peptides and their overall charge at different pH. The chargeable amino acids are underlined. FIG. 5B, pH dependence of the Ires % for the four peptides (cis) shown in a using type II W116S-FraC nanopores under −30 mV applied potential. FIG. 5C, Comparison of the Ires % versus the mass of peptides at pH 4.5 and 3.8. FIG. 5D, Voltage dependence of c-Myc dwell times at different pHs. All electrophysiology measurements were carried out in 1 M KCl, 0.1 M citric acid, and pH was adjusted with 1 M Tris base to desired values. 50 kHz sampling rate and 10 kHz filter was used for collecting the current events. Error bars are standard deviations obtained from at least three measurements. The charges of the peptides were calculated according to the pKa for individual amino acids[36]. FIG. 5A discloses SEQ ID NOS 14-15, 17 and 20, respectively, in order of appearance.

Figures 6A, 6B:
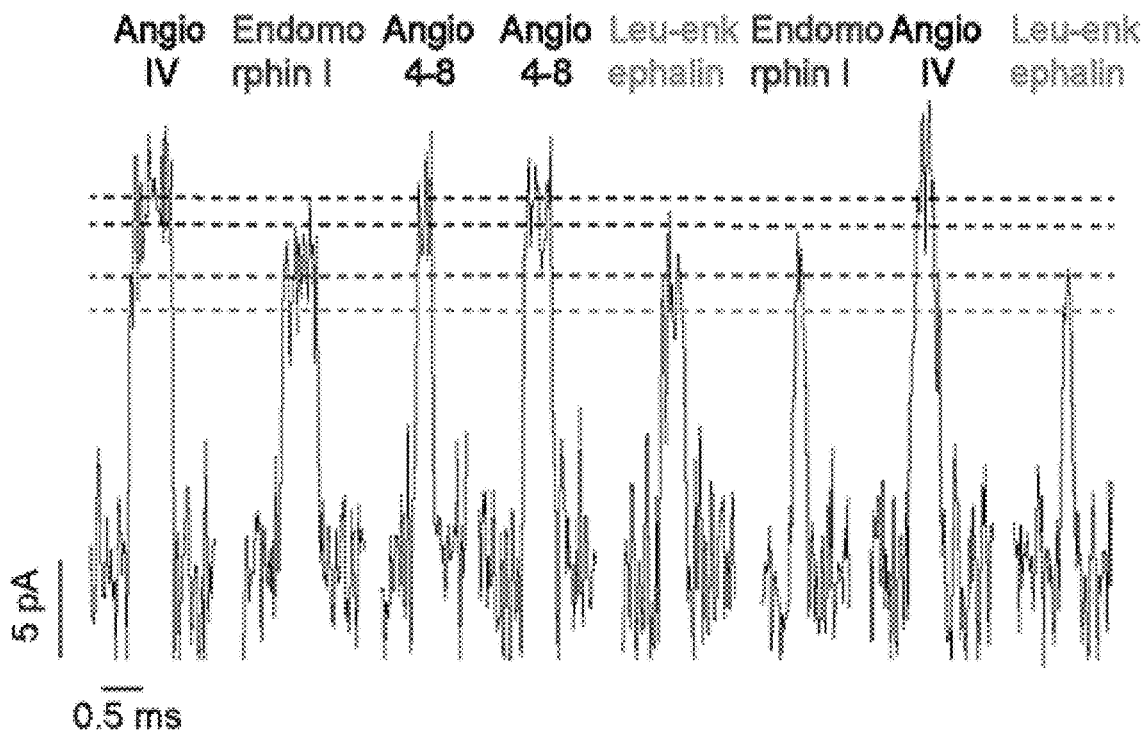
Figure 6C:
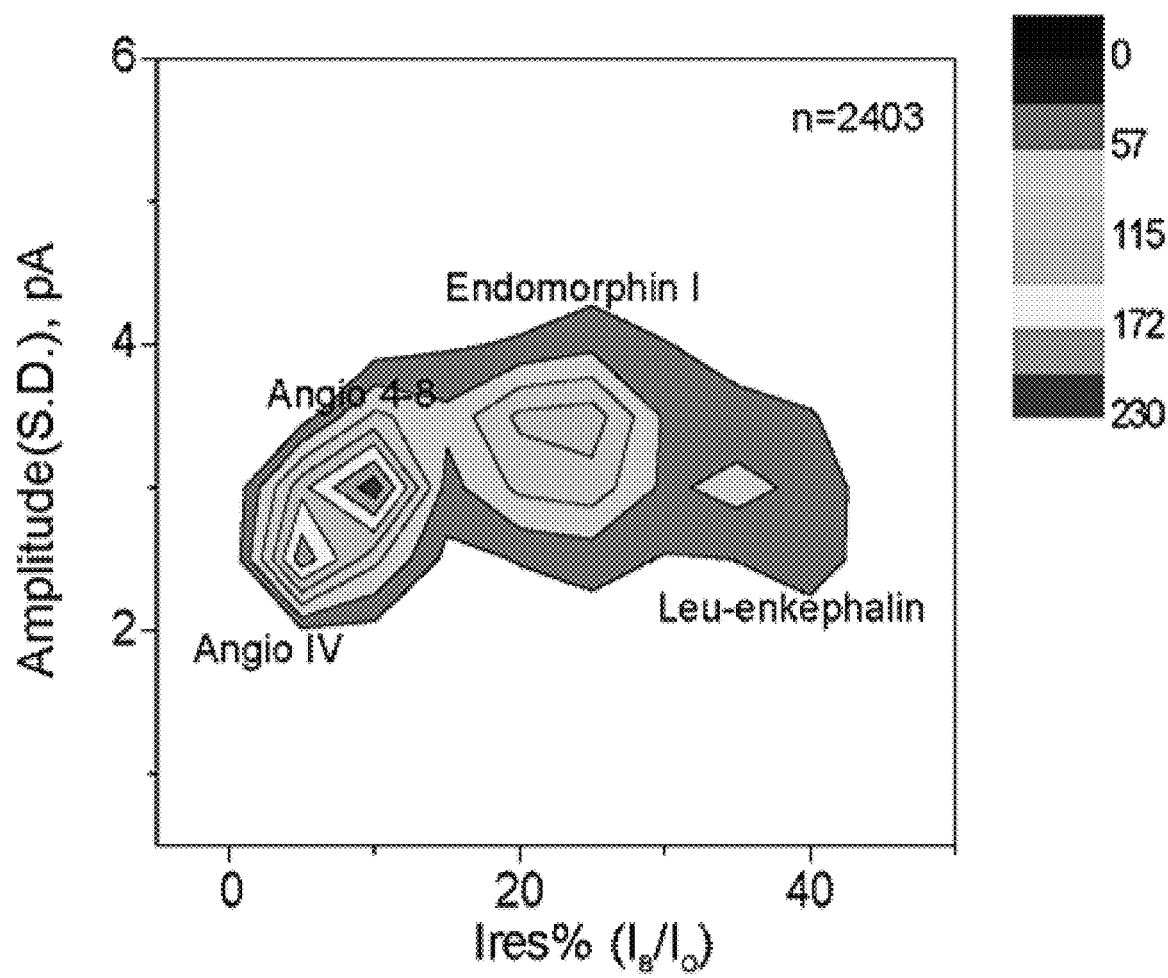

FIGS. 6A-6C: Discrimination of short peptide mixture with type III FraC nanopores comprising mutant W112S-W116S-FraC. FIG. 6A, Sequence, Ires % (~50 mV) and MW of angiotensin IV, angiotensin 4-8, endomorphin I and leucine enkephalin. FIG. 6B, Typical blockades provoked by the different peptides. FIG. 6C, Color density plot showing the Ires % versus the standard deviation of the current blockade for the mixture of angiotensin IV, angiotensin 4-8, endomorphin I and leucine-enkephalin. All measurements and recordings were performed in pH 4.5 buffer containing 1 M KCl, 0.1 M citric acid, 180 mM Tris base with a 50 kHz sampling and 10 kHz filter. Standard deviations were calculated from three repeats at least. FIG. 6A discloses SEQ ID NOS 22-24 and 26, respectively, in order of appearance.

Figure 7A:
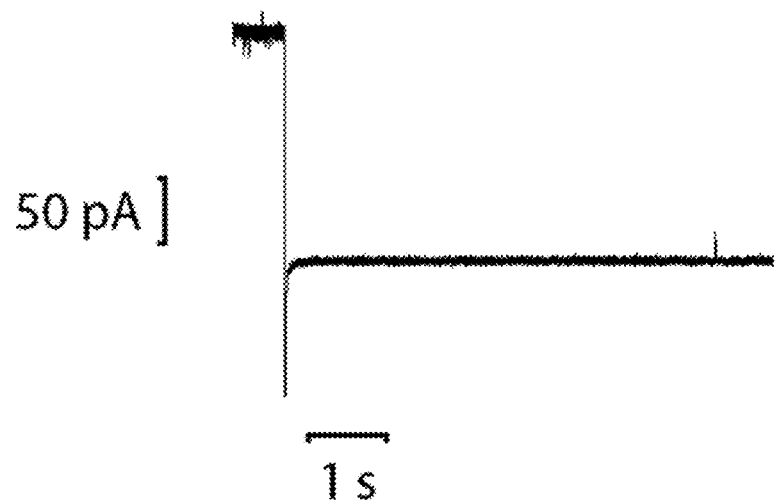
Figure 7B:
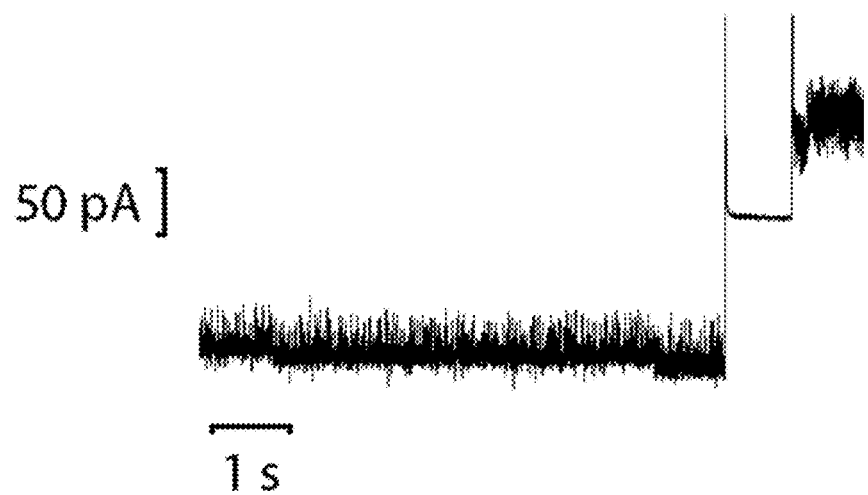

FIGS. 7A-7B. Characterization of type II FraC nanopores comprising an oxidized cysteine at position 10. Difference between the D10C/W116S type II pore (FIG. 7A) and the oxidized D10C/W116S type II pore (FIG. 7B). Recordings were performed in a buffer containing 1 M NaCl, pH 7.5, ±50 mV.

EXPERIMENTAL SECTION

Materials and Methods
Chemicals

Endothelin 1 (≥97%, CAS #117399-94-7), endothelin 2 (≥97%, CAS #123562-20-9), dynorphin A porcine (≥95%, CAS #80448-90-4), angiotensin I (90%, CAS #70937-97-2), angiotensin II (≥93%, CAS #4474-91-3), c-Myc 410-419 (≥97%, #M2435), Asn1-Val5-Angiotensin II (≥97%, CAS #20071-00-5), Ile7 Angiotensin III (≥95%, #A0911), leucine enkephalin (≥95%, #L9133), 5-methionine enkephalin (≥95%, CAS #82362-17-2), endomorphin I (≥95%, CAS #189388-22-5), pentane (≥99%, CAS #109-66-0), hexadecane (99%, CAS #544-76-3), Trizma®hydrochloride (≥99%, CAS #1185-53-1), Trizma®base (≥99%, CAS #77-86-1), Potassium chloride (≥99%, CAS #7447-40-7), N,N-Dimethyldodecylamine N-oxide (LADO, ≥99%, CAS #1643-20-5) were obtained from Sigma-Aldrich. Pre angiotensin 1-14 (≥97%, #002-45), angiotensin 1-9 (≥95%, #002-02), angiotensin A (≥95%, #002-36), angiotensin 1-7 (≥95%, #002-31), angiotensin IV (≥95%, #002-28) were purchased from Pheonix Pharmaceuticals. Angiotensin 4-8 (≥95%) was synthesized by BIOMATIK. 1,2-diphytanoyl-sn-glycero-3-phosphocholine (DPhPC, #850356P) and sphingomyelin (Porcine brain, #860062) were purchased from Avanti Polar Lipids. Citric acid (99.6%, CAS #77-92-9) was obtained from ACROS. n-Dodecyl (3-D-maltoside (DDM, ≥99.5%, CAS #69227-93-6) was bought from Glycon Biochemical EmbH. DNA primers were synthesized from Integrated DNA Technologies (IDT), enzymes from Thermo scientific. All peptides were dissolved with Milli-Q water without further purification and stored in −20° C. freezer. pH 7.5 buffer containing 15 mM Tris in this study was prepared by dissolving 1.902 g Trizma® HCl and 0.354 g Trizma® base in 1 litre Milli-Q water (Millipore, Inc).

FraC Monomer Expression and Purification

FraC gene containing NcoI and HindIII restriction site at the 5' and 3' ends, respectively, and a sequence encoding for a poly histidine tag at the 3' terminus was cloned to a pT7-SC1 plasmid. Plasmids were transformed into BL21 (DE3) E.cloni® competent cell by electroporation. Cells were grown on LB agar plate containing 100 μg/mL ampicillin overnight at 37° C. The entire plate was then harvested and inoculated into 200 mL fresh 2YT media and the culture was grown with 220 rpm shaking at 37° C. until the optical density at 600 nm of the cell culture reached 0.8. Then 0.5 mM IPTG was added to the media and the culture was transferred to 25° C. for overnight growth with 220 rpm shaking. The next day the cells were centrifuged (2000×g, 30 minutes) and the pellet stored at −80° C. Cell pellets harvested from 100 mL culture media were used to purify FraC monomer. 30 mL of cell lysis buffer (150 mM NaCl, 15 mM Tris, 1 mM $MgCl_2$, 4 M urea, 0.2 mg/mL lysozyme and 0.05 unit/mL DNase) was added to resuspend the pellet and vigorously mixed for 1 hour. Cell lysate was then sonicated with Branson Sonifier 450 for 2 minutes (duty cycle 10%, output control 3). Then the crude lysate was centrifuged down at 4° C. for 30 minutes (5400×g), and the supernatant incubated with 100 μL Ni-NTA beads (Qiagen) for 1 hour with gentle shaking. Beads were spun down and loaded to a Micro Bio-spin column (Bio-rad). 10 mL of SDEX buffer (150 mM NaCl, 15 mM Tris, pH 7.5) containing 20 mM imidazole was used to wash the beads, and proteins were eluded with 150 μL elution buffer (SDEX buffer, 300 mM imidazole). The concentration of protein was measured by measuring the absorption at 280 nm with Nano-drop 2000 (Thermo scientific) using the elution buffer as blank. To further confirm the purity of monomer, monomeric FraC was diluted to 0.5 mg/mL using the elution buffer and 9 μL of the diluted sample was mixed with 3 μL of 4× loading buffer (250 mM Tris HCl, pH 6.8. 8% SDS, 0.01% bromophenol blue and 40% glycerol) and then loaded to 12% SDS-PAGE gel. Gels were run for 30 min with 35 mA constant applied current, and stained with coomassie dye (InstantBlue™, Expdedeon) for more than 1 hour before viewing using a gel imager (Gel Doc™, Bio-rad).

≥FraC|B9W5G6 (amino acid sequence)
SADVAGAVIDGAGLGFDVLKTVLEALGNVKRKIAVGIDNESGKTWTAMNTY

FRSGTSDIVLPHKVAHGKALLYNGQKNRGPVATGVVGVIAYSMSDGNTLAV

LFSVPYDYNWYSNWWNVRVYKGQKRADQRMYEELYYHRSPFRGDNGWHSRG

LGYGLKSRGFMNSSGHAILEIHVTKA

6×His-WtFraC (amino acid sequence) as used in the present invention. Bold residues indicate residues of the N- and C-terminal end that were added to the original sequence.

MASADVAGAVIDGAGLGFDVLKTVLEALGNVKRKIAVGIDNESGKTWTAMN
TYFRSGTSDIVLPHKVAHGKALLYNGQKNRGPVATGVVGVIAYSMSDGNTL
AVLFSVPYDYNWYSNWWNVRVYKGQKRADQRMYEELYYHRSPFRGDNGWHS
RGLGYGLKSRGFMNSSGHAILEIHVTKAGSAHHHHHH

>6xHis-WtFraC (DNA sequence)
ATGGCGAGCGCCGATGTCGCGGGTGCGGTAATCGACGGTGCGGGTCTGGGC
TTTGACGTACTGAAAACCGTGCTGGAGGCCCTGGGCAACGTTAAACGCAAA
ATTGCGGTAGGGATTGATAACGAATCGGGCAAGACCTGGACAGCGATGAAT
ACCTATTTCCGTTCTGGTACGAGTGATATTGTGCTCCCACATAAGGTGGCG
CATGGTAAGGCGCTGCTGTATAACGGTCAAAAAAATCGCGGTCCTGTCGCG
ACCGGCGTAGTGGGTGTGATTGCCTATAGTATGTCTGATGGGAACACACTG
GCGGTACTGTTCTCCGTGCCGTACGATTATAATTGGTATAGCAATTGGTGG
AACGTGCGTGTCTACAAAGGCCAGAAGCGTGCCGATCAGCGCATGTACGAG
GAGCTGTACTATCATCGCTCGCCGTTTCGCGGCGACAACGGTTGGCATTCC
CGGGGCTTAGGTTATGGACTCAAAAGTCGCGGCTTTATGAATAGTTCGGGC
CACGCAATCCTGGAGATTCACGTTACCAAAGCAGGCTCTGCGCATCATCAC
CACCATCACTGATAAGCTT FraC Mutation Preparation FraC mutants were prepared according to MEGAWHOP method. 25 μL REDTaq® ReadyMix™ was mixed with 4 μM primer (see Table 1) containing the desired mutation with 50 ng plasmid (pT7-SC1 with wild type FraC gene) as template and the final volume was brought to 50 μL with MilliQ water.

TABLE 1

Primer sequences used in this study for preparing FraC mutants.

| Primer name | DNA sequences |
|---|---|
| T7 promoter | 5' TAATACGACTCACTATAGGG 3' |
| T7 terminator | 5' GCTAGTTATTGCTCAGCGG 3' |
| W112S Fw | 5' ACGATTATAATAGCTATAGCAATTGGTGG 3' |
| W116S Fw | 5' ATTGGTATAGCAATAGCTGGAACGTG 3' |
| W112116S Fw | 5' GTACGATTATAATAGCTATAGCAATAGCTGGA ACGTGC 3' |
| D109S ReV | 5' TGCTATACCAATTATAGCTGTACGGCA 3' |

The PCR protocol was initiated by 150 seconds denature step at 95° C., followed by 30 cycles of denaturing (95° C., 15 s), annealing (55° C., 15 s), and extension (72° C., 60 s). The PCR products (MEGA primer) were combined and purified using a QIAquick PCR purification kit with final DNA concentration around 200 ng/μL. The second PCR was performed for whole plasmid amplification. 2 μL of MEGA primer, 1 μL Phire II enzyme, 10 μL 5× Phire buffer, 1 μL 10 mM dNTPs, were mixed with PCR water to 50 μL final volume. PCR started with pre-incubated at 98° C. (30 s) and then 25 cycles of denaturing (98° C., 5 s), annealing (72° C., 90 s), extension (72° C., 150 s). When the PCR was completed, 1 μL Dpn I enzyme was added and the mixture kept at 37° C. for 1 hour. Then the temperature was raised to 65° C. for 1 minute to inactivate the enzyme. Products were then transformed into E. cloni® 10G cells (Lucigen) competent cell by electroporation. Cells were plated on LB agar plates containing 100 μg/mL ampicillin and grew at 37° C. overnight. Single clones were enriched and sent for sequencing.

Sphingomyelin-DPhPC Liposome Preparation 20 mg sphingomyelin and 20 mg DPhPC (1,2-diphytanoyl-sn-glycero-3-phosphocholine) were dissolved in 4 mL pentane with 0.5% v/v ethanol and brought to a 50 mL round flask. The solvent was then evaporated by rotation and using a hair-dryer to warm-up the flask. After evaporation, the flask was kept at ambient temperature for an additional 30 minutes. The lipid film was resuspended with 4 mL SDEX buffer (150 mM NaCl, 15 mM Tris, pH 7.5) and the solution immersed in a sonication bath for 5 minutes. Liposome suspensions were stored at −20° C.

FraC Oligomerization

FraC oligomerization was triggered by incubation of FraC monomers with sphingomelyin-DPhPC liposomes. Frozen liposome were thawed and sonicated in a water bath for one minute. FraC monomers were diluted to one mg/mL using SDEX buffer, and then 50 μL of FraC monomers were added to 50 μl of a 10 mg/mL liposome solution to obtain a mass ratio of 10:1 (liposome:protein). The lipoprotein solution was incubated at 37° C. for 30 min to allow oligomerization. Then 10 μl of 5% (w/v, 0.5% final) LADO was added to the lipoprotein solution to solubilize the liposomes. After clarification (typically 1 minute) the solution was transferred to a 50 mL Falcon tube. Then 10 mL of SDEX buffer containing 0.02% DDM and 100 μL of pre-washed Ni-NTA beads were added to the Falcon tube and mixed gently in shaker for 1 hour at room temperature. The beads were then spun down and loaded to a Micro Bio-spin column. 10 mL wash buffer (150 mM NaCl, 15 mM Tris, 20 mM imidazole, 0.02% DDM, pH 7.5) was used to wash the beads and oligomers eluded with 100 µL elution buffer (typically 200 mM EDTA, 75 mM NaCl, 7.5 mM Tris pH 7.5, 0.02% DDM). The FraC oligomers were stored at 4° C. Under these conditions the nanopores are stable for several months.

W112S-W116S-FraC Oligomer Separation with His-Trap Chromatography

200 µL of W112S-W116S-FraC monomers (3 mg/mL) were incubated with 300 µL of Sphingomyelin-DPhPC liposome (10 mg/mL) and kept at 4° C. for 48 hours after which 0.5% LADO (final concentration) was added to solubilize the lipoprotein. Then the buffer was exchanged to the 500 mM NaCl, 15 mM Tris, 0.01% DDM, 30 mM imidazole, pH 7.5 (binding buffer) using a PD SpinTrap G-25 column. W112S-W116S-FraC oligomers were then loaded to Histrap HP 1 mL column (General Electric) using an AKTA pure FPLC system (General Electric). The loaded oligomers were washed with 10 column volumes of 500 mM NaCl, 15 mM Tris, 0.01% DDM, 30 mM imidazole, pH 7.5, prior applying an imidazole gradient (from 30 mM to 1 M imidazole, 500 mM NaCl, 15 mM Tris, 0.01% DDM, pH 7.5) over 30 column volumes. The signal was monitored with the absorbance at 280 nm and fractions were collected when the absorbance was higher than 5 mAu.

Electrophysiology Measurement and Data Analysis

Electrical recordings were performed as explained in details previously[27,37]. $I_O$, referring to open pore current, were measured by fitting Gaussian functions to event amplitude histograms. Residual current values (Ires %) were calculated by dividing the blockade current ($I_B$) by open pore current ($I_B/I_O \times 100\%$). Dwell times and inter-event times were measured by fitting single exponentials to histograms of cumulative distribution.

Ion Permeability Measurement

In order to measure reversal potentials, a single channel was obtained under symmetric conditions (840 mM KCl, 500 µL in each electrophysiology chamber) and the electrodes were balanced. The 400 µL of a buffered stock solution of 3.36 M KCl was slowly added to cis chamber, while 400 µL of salt free buffered solution was added to the trans chamber to obtain a total volume of 900 µL (trans:cis, 467 mM KCl:1960 mM KCl). After the equilibrium was reached, IV curves were collected from −30 to +30 mV. The resulting voltage at zero current is the reversal potential (Vr). The ion selectivity ($P_K^+/P_{Cl}^-$) was then calculated using the Goldman-Hodgkin-Katz equation (equation 1) where $[a_{K^+/Cl^-}]_{cis/trans}$ is the activity of the $K^+$ or $Cl^-$ in the cis or trans compartment, R the gas constant, T the temperature and F the Faraday's constant.

$$\frac{P_{K^+}}{P_{Cl^-}} = \frac{[a_{Cl^-}]_{trans} - [a_{Cl^-}]_{cis} e^{V_r F/RT}}{[a_{K^+}]_{trans} e^{V_r F/RT} - [a_{K^+}]_{cis}} \qquad (1)$$

The activity of ions was calculated by multiplying the molar concentration of the ion for the mean ion mobility (0.649 for 500 mM KCl, and 0.573 for 2000 mM). Ag/AgCl electrodes were surrounded by 2.5% agarose bridge in 2.5 M NaCl.

Molecular Models of Type I, II and III FraC Nanopores

The 3D models with different multimeric order, ranging from five to nine monomers, were constructed with the symmetrical docking function of Rosetta[38]. A monomer without lipids was extracted from the crystal structure of FraC with lipids (PDB_ID 4tsy). Symmetrical docking arranged this monomer around a central rotational axis ranging in order form 5 to 9. In total Rosetta generated and scored 10 000 copies for each symmetry. In all cases, a multimeric organization with a symmetry similar to the crystal structure could be identified as a top scoring solution. However, in the pentameric assembly the multimer interface was not fully satisfied as compared to the crystal structure, with large portions left exposed. The 9-fold symmetric model however exhibited a significant drop in Rosetta score compared to the 6- 7- and 8-fold symmetric models indicating an unfavored assembly of the nonameric assembly with the 6-7- and 8-fold assemblies as the most plausible. To create lipid bound models, the crystal structure with lipids was superimposed on each monomer of the generated models, allowing the lipid coordinates to be transferred. The residues within 4.5 angstrom of the lipids were minimized with the Amber10 force field.

Example 1: Engineering the Size of FraC Nanopores

One of the main challenges in biological nanopores analysis is to obtain nanopores with different size and shape. Most of biological nanopores are formed by multiple repeats of individual monomers. Hence, different nanopore sizes might be obtained by engineering the protein oligomeric composition[28]. We noticed that at pH 7.5 a small fraction of Wild Type FraC (WT-FraC) nanopores showed a lower conductance (1.26±0.08 nS, −50 mV, type II WT-FraC, FIG. 1B) compared to the dominant fraction (2.26±0.08 nS, −50 mV, type I WT-FraC), suggesting that FraC might be able spontaneously to assemble into nanopores with smaller size. At pH 4.5 yet a smaller nanopore conductance was observed (0.42±0.03 nS, type III WT-FraC, −50 mV, FIG. 1B). We noticed that the reconstitution of lower conductance nanopores depended to several purification conditions. In particular, we observed that the occurrence of type II and type III nanopores increased when the oligomers were stored in solution for several weeks or when the concentration of monomeric WT-FraC was reduced during oligomerisation.

In an attempt to enrich for type II and type III FraC nanopores, the interaction between the nanopore and the lipid interface was weakened by substituting W112 and W116 at the lipid interface of FraC (FIG. 1A) with serine. The inventors reasoned that a lower concentration of monomers during liposome-triggered oligomerisation would increase the population of lower molecular mass oligomers. Surprisingly, it was found that at pH 4.5 using W116S-FraC and W112S-W116S-FraC oligomers, type II and type III FraC nanopores were the dominant species, respectively (FIG. 1B, FIG. 2). Conveniently, the different nanopore types could be separated by Ni-NTA affinity chromatography using an imidazole gradient. Furthermore, it was found that enrichment of type II and type III FraC nanopores could also be obtained at pH 7.5 by replacing aspartate 109 at the lipid interface with serine (see FIG. 2E, Table 2).

TABLE 2 relative amounts of Type I, Type II and Type III for each of the
FraC nanopores investigated at neutral and acidic pH.

|  |  | Type I(%) | SD | Type II(%) | SD | Type III(%) | SD |
|---|---|---|---|---|---|---|---|
| pH 7.5 | Wild type | 85.7 | 3.8 | 14.3 | 3.8 | 0.0 | 0.0 |
|  | W112S | 61.9 | 4.3 | 38.1 | 4.3 | 0.0 | 0.0 |
|  | W116S | 61.1 | 5.7 | 38.9 | 5.7 | 0.0 | 0.0 |
|  | W112116S | 27.1 | 3.9 | 72.9 | 3.9 | 0.0 | 0.0 |
|  | D109S | 50.3 | 3.8 | 48.0 | 3.6 | 1.7 | 1.5 |
|  | D109SW116S | 29.3 | 9.5 | 66.7 | 8.4 | 4.0 | 4.0 |
| pH 4.5 | Wild type | 42.5 | 10.6 | 51.9 | 7.7 | 5.6 | 7.9 |
|  | W116S | 29.0 | 4.0 | 47.0 | 4.6 | 24.0 | 2.3 |
|  | W112SW116S | 21.7 | 4.7 | 38.0 | 8.5 | 40.3 | 9.3 |
|  | D109S | 35.7 | 2.1 | 56.3 | 9.1 | 8.0 | 7.0 |
|  | D109SW116S | 19.3 | 8.4 | 64.3 | 6.7 | 16.3 | 3.2 |

Among FraC nanopores of the same type, the lipid interface modifications caused by W112S and W116S substitutions did not alter the conductance and ion selectivity as compared to that of wild type (FIG. 1C, FIG. 2, Table 3) suggesting that the modifications did not altered the overall fold of the nanopores. When characterised in lipid bilayers, type I, type II and type III nanopores showed a well-defined single conductance distribution and a steady open pore current (FIGS. 1D-1E).

Interestingly, Type I, Type II and Type III nanopores showed increasing cation selectivity (from 2.0 for type I to 4.2 for type III W116S-FraC nanopores at pH 4.5 (FIG. 1F, Table 3), most likely reflecting a larger overlap of the electrical double layer in the nanopores with a narrower constriction.

These findings strongly suggest that the three types of FraC nanopores represent nanopores with different protomeric compositions. Molecular modelling allowed predicting the diameter of type II (1.1 nm) and type III (0.8 nm) nanopores (FIG. 1G); and revealed that type III FraC is most likely the biological nanopore with the smallest constriction known to date.

Example 2: Identification of Peptides Containing Single Amino Acid Substitutions Using Type II or Type III FraC Nanopores as Sensor Type II FraC nanopores were used to sample a series of angiotensin peptides (which in blood regulate blood pressure and fluid balance. The peptides were added to the cis side of

TABLE 3

Ion selectivity of different FraC pores at pH 7.5 and 4.5.

|  |  | pH 7.5 | | pH 4.5 | |
|---|---|---|---|---|---|
|  |  | Reversal potential (mV) | $P_{K^+}/P_{Cl^-}$ | Reversal potential (mV) | $P_{K^+}/P_{Cl^-}$ |
| WT-FraC | Type I | 17.2 ± 1.2 | 3.6 ± 0.4 | 10.5 ± 1.4 | 2.1 ± 0.2 |
|  | Type II | 20.8 ± 1.6 | 5.2 ± 0.9 | 12.3 ± 1.2 | 2.4 ± 0.2 |
|  | Type III | / | / | 20.6 ± 1.1 | 5.0 ± 0.6 |
| W116S-FraC | Type I | / | / | 10.1 ± 0.9 | 2.0 ± 0.1 |
|  | Type II | / | / | 12.8 ± 0.7 | 2.5 ± 0.2 |
|  | Type III | / | / | 18.8 ± 0.5 | 4.2 ± 0.2 |
| W112S-W116S-FraC | Type I | / | / | 8.8 ± 1.2 | 1.9 ± 0.2 |
|  | Type II | / | / | 14.0 ± 0.1 | 2.8 ± 0.1 |
|  | Type III | / | / | 20.1 ± 0.6 | 4.8 ± 0.3 |

The ion selectivity ($P_{K^+}/P_{Cl^-}$) was calculated from the reversal potential according to the Goldman-Hodgkin-Katz equation:

$$\frac{P_{K^+}}{P_{Cl^-}} = \frac{[a_{Cl^-}]_{trans} - [a_{Cl^-}]_{cis} e^{V_r F/RT}}{[a_{K^+}]_{trans} e^{V_r F/RT} - [a_{K^+}]_{cis}},$$

where Vr is the reversal potential, $P_{K^+}/P_{Cl^-}$ the ion selectivity, a the activity of ions and F the Farady constant. Electrophysiology recordings were carried out with 1960 mM KCl in the cis solution and 467 mM KCl in the trans solution. The activity of ions was calculated by multiplying the molar concentration of the ion for the mean ion mobility (0.649 for 500 mM KCl, and 0.573 for 2000 mM)[3]. Errors are given as standard deviations calculated from 3 experiments at least.

type II W116S-FraC nanopores and the induced ionic current blockades ($I_B$) was measured. Residual currents percent (Ires %, defined as $I_B/I_O \times 100$) were used instead of current blockades because they provided more reliable values when comparing different nanopores. Results are shown in FIG. 3A and Table 4.

Angiotensin I (DRVYIHPFHL (SEQ ID NO: 14), 1296.5 Da), showed the deepest blockade (Ires %=8.8±0.2) and angiotensin IV (VYIHPF (SEQ ID NO: 22), 774.9 Da) the shallowest blockade (Ires %=38.9±4.0). The residual current of angiotensin II (DRVYIPF (SEQ ID NO: 17), 1046.2 Da, Ires %=17.9±1.3) and angiotensin III (RVYIIPF (SEQ ID NO: 20), 931.1 Da, Ires %=22.1±0.5) fell at intermediate values. When the four peptides were tested simultaneously, individual peptides could be readily discriminated (FIG. 3A).

TABLE 4

Peptide analysis using different types of FraC nanopores at pH 4.5

| Peptide | Sequence | Molecular weight (g/mol) | pH 7.5 | pH 4.5 | Ires % ($I_B/I_O$) % pH4.5 | Dwell time (ms) |
|---|---|---|---|---|---|---|
| WT-FraC type I pore, −30 mV | | | | | | |
| Endothelin 2 | CSCSSWLDKECVYFCHLDIIW | 2546.9 | −2.15 | 0.36 | 6.1 ± 1.8 | 104.0 ± 29.9 |
| Endothelin 1 | CSCSSLMDKECVYFCHLDIIW | 2491.9 | −2.15 | 0.36 | 7.5 ± 0.5 | 19.73 ± 1.95 |
| Dynorphin A | YGGFLRRIRPKLKWDNQ | 2147.5 | 3.76 | 4.48 | 15.1 ± 2.6 | 3.68 ± 0.76 |
| Pre angiotensinogen | DRVYIHPFHLVIHN | 1758.9 | 0.03 | 3.45 | 24.6 ± 2.3 | 0.29 ± 0.04 |
| Angiotensin I | DRVYIHPFHL | 1296.5 | −0.06 | 2.46 | 43.4 ± 0.9 | 0.15 ± 0.04 |
| W116S-FraC type II pore, −30 mV | | | | | | |
| Angiotensin I | DRVYIHPFHL | 1296.5 | −0.06 | 2.46 | 8.8 ± 0.2 | 0.54 ± 0.01 |
| c-Myc 410-419 | EQKLISEEDL | 1203.3 | −3.24 | −1.19 | 30.0 ± 3.4 | 0.12 ± 0.01 |
| Angiotensin 1-9 | DRVYIHPFH | 1183.3 | −0.06 | 2.46 | 14.0 ± 0.2 | 0.37 ± 0.04 |
| Angiotensin II | DRVYIHPF | 1046.2 | −0.15 | 1.47 | 17.9 ± 1.3 | 0.37 ± 0.04 |
| Asn1Val5 | | | | | | |
| Angiotensin II | NRVYVHPF | 1031.2 | 0.85 | 2.03 | 19.6 ± 0.2 | 0.34 ± 0.06 |
| Angiotensin A | ARVYIHPF | 1002.2 | 0.85 | 2.03 | 21.0 ± 0.6 | 0.34 ± 0.02 |
| Angiotensin III | RVYIHPF | 931.1 | 0.85 | 2.03 | 22.1 ± 0.5 | 0.35 ± 0.04 |
| Ile7 Angiotensin III | IRVYIHPI | 897.1 | 0.85 | 2.03 | 24.3 ± 0.4 | 0.19 ± 0.05 |
| Angiotensin IV | VYIHPF | 774.9 | −0.15 | 1.02 | 38.9 ± 4.0 | 0.15 ± 0.06 |
| W112S-W116S-FraC type III pore, −50 mV | | | | | | |
| Angiotensin IV | VYIHPF | 774.9 | −0.15 | 1.02 | 1.1 ± 0.8 | 0.61 ± 0.07 |
| Angiotensin 4-8 | YIHPF | 675.8 | −0.15 | 1.02 | 8.2 ± 0.4 | 0.40 ± 0.04 |
| Endomorphin I | YPWF | 610.7 | −0.24 | 0.04 | 19.2 ± 0.5 | 0.32 ± 0.04 |
| Met5 Enkephalin | YGGFM | 573.7 | −0.24 | 0.04 | 33.5 ± 0.7 | 0.16 ± 0.02 |
| Leucine Enkephalin | YGGFL | 555.6 | −0.24 | 0.04 | 34.5 ± 2.4 | 0.20 ± 0.05 |

The electrophysiology solution contained 1M KCl, 0.1M citric acid, 180 mM Tris base at pH 4.5.
Recordings were performed using a 50 kHz sampling and applying 10 kHz Bassel filter.
Standard deviations were obtained for at least three measurements.
The charges of the peptides were calculated according to the $pK_a$ for individual amino acid[36].

The resolution limit of the nanopore sensor was challenged by sampling a mixture of peptides. Remarkably, angiotensin II and angiotensin A, having an identical composition except for the initial amino acid (aspartate in angiotensin II vs. alanine in angiotensin A), appeared as distinctive peaks in Ires % plots (FIG. 3B). Smaller differences in peptide mass, e.g. the 34 Da difference between phenylalanine and leucine in angiotensin III and Ile7 angiotensin III, were observed but not easily detected (data not shown), indicating the resolution of our system at ~40 Da. Smaller peptides such as angiotensin II 4-8 (YIHPF (SEQ ID NO: 23), 675.8 Da), endomorphin I (YPWF (SEQ ID NO: 24), 610.7 Da) or leucine enkephalin (YGGFL (SEQ ID NO: 26), 555.6 Da) translocated too quickly across type II W116S-FraC nanopores to be sampled. However, they could be readily measured using type III W112S-W116S-FraC nanopores (Table 4; FIGS. 6A-6C).

Example 3: A Nanopore Mass Spectrometer for Peptides

Although the ability of biological nanopores to distinguish between known analytes is useful, a more powerful application would be the identification of peptide masses directly from ionic current blockades without holding prior knowledge of the analyte identity. In an effort to assess FraC nanopores as peptide mass analyzer, additional peptides were tested at pH 4.5 and 1 M KCl using type I, type II and type III FraC nanopores (FIGS. 4A-4C, Table 4). Crucially, analytes with largely different charge compositions were included.

It was found that for most of peptides there was a direct correlation between the size and the residual current (FIGS. 4A-4C). A notable exception was c-Myc 410-419 (1203.3 Da), an intentionally selected peptide because it includes a long stretch of negatively charged residues (FIG. 5A). The overall negative charge of the peptide at pH 4.5 (see Table 4) was expected to have an effect on both peptide capture and recognition. c-Myc 410-419 could be readily captured at negative applied potentials (trans), indicating that the cis to trans electroosmotic flow across the nanopore can overcome the electrostatic energy barrier opposing peptide capture. However, the Ires % of c-Myc 410-419 (30.0±3.4) was significantly higher than the expected value (FIG. 4b).

We reasoned that such anomaly might be due to the interaction between the acidic amino acids of the peptide and the negatively charged constriction of FraC nanopores. Thus, we lowered the pH solution to values where the aspartate and glutamate side chains in the peptides are expected to be protonated, hence become neutral (FIG. 5A). Rewardingly, at pH 3.8, the signal corresponding to c-Myc 410-419 (1203.3 Da) fell between the signal of angiotensin I (1296.5 Da), and angiotensin II (1046.2 Da, FIGS. 5B-5C). This indicates that, after losing its negative charges, the peptide blockades scaled with the expected mass of the peptides.

It has been assumed[1,30,31] and experimentally proven[32] that the voltage dependence of the average dwell time (off) can report on the translocation of a molecule across a nanopore. Under a negative bias (trans) for positively charged peptides (added in cis) both electrophoretic and electroosmotic forces (from cis to trans) promote the entry and translocation[27] across the nanopore. For negatively charged peptides, such as c-Myc 410-419 at pH 4.5 (FIG. 5A), the electroosmotic driving force must be stronger than the opposing electrophoretic force. The voltage dependence of $\tau_{off}$ was examined for c-Myc 410-419 at different pH values (FIG. 5D). At pH 4.5 the peptide exhibited a maximum in $\tau_{off}$ at −50 mV, suggesting that at low potentials c-Myc 410-419 returns to the cis chamber (<50 mV), and at higher potentials (≥50 mV) c-Myc 410-419 exits to the trans chamber. At pH 3.8 and lower, we observed a decrease in $\tau_{off}$ at higher potentials, indicating that c-Myc 410-419 crosses the membrane to the trans chamber.

As shown in FIGS. 6A-6C, type III FraC nanopore can detect differences in peptide length down to 4 amino acids (mass around 500 Dalton) in a peptide mixture. It was also found that the residual current signal correlated well with the mass of peptides, suggesting that Type III can be used as a detector for a peptide having a mass down to ~500 Da.

Example 4: Peptide Mass Identifier at pH 3

This example shows that mutation D10C can be used as additional mutation to obtain a FraC pore showing a quiet signal in electrophysiology recordings.

Using mutant W116S as exemplary mutant, the aspartic acid at position 10 of FraC was converted to cysteine by site-directed mutagenesis. The thiol group of cysteine was then oxidized to sulfonic acid by incubation of FraC monomers with 10% hydrogen peroxide (v/v), which was dissolved in regular buffer (e.g. 10 mM Tris buffer pH 7.5, 150 mM NaCl). As a control, the double mutant was left without oxidation.

D10C/W116S FraC was oligomerized, and the oligomers tested in electrical recordings. FIGS. 7A-7B shows the trace comparison between the D10C/W116S pore and oxidized D10C/W116S pore to demonstrate the difference after oxidization. Oligomerised pores from oxidized D10C/W116S FraC monomers showed a quiet signal in electrophysiology recordings, as compared to a more noisy signal observed for nanopores that had not been subjected to oxidation.

REFERENCES

1. Clarke, J. et al. Continuous base identification for single-molecule nanopore DNA sequencing. *Nat. Nanotechnol.* 4, 265-270 (2009).
2. Derrington, I. M. et al. Nanopore DNA sequencing with MspA. *Proc. Natl. Acad. Sci.* 107, 16060-16065 (2010).
3. Bezrukov, S. M., Vodyanoy, I., Brutyan, R. A. & Kasianowicz, J. J. Dynamics and free energy of polymers partitioning into a nanoscale pore. *Macromolecules* 29, 8517-8522 (1996).
4. Robertson, J. W. F. et al. Single-molecule mass spectrometry in solution using a solitary nanopore. *Proc. Natl. Acad. Sci.* 104, 8207-8211 (2007).
5. Baaken, G. et al. High-Resolution Size-Discrimination of Single Nonionic Synthetic Polymers with a Highly Charged Biological Nanopore. *ACS Nano* 9, 6443-6449 (2015).
6. Aksoyoglu, M. A. et al. Size-dependent forced PEG partitioning into channels: VDAC, OmpC, and α-hemolysin. *Proc. Natl. Acad. Sci.* 113, 9003-9008 (2016).
7. Krasilnikov, O. V., Rodrigues, C. G. & Bezrukov, S. M. Single polymer molecules in a protein nanopore in the limit of a strong polymer-pore attraction. *Phys. Rev. Lett.* 97, 1-4 (2006).
8. Oukhaled, A. G., Biance, A. L., Pelta, J., Auvray, L. & Bacri, L. Transport of long neutral polymers in the semidilute regime through a protein nanopore. *Phys. Rev. Lett.* 108, 1-4 (2012).
9. Zhao, Q., Jayawardhana, D. A., Wang, D. & Guan, X. Study of peptide transport through engineered protein channels. *J. Phys. Chem. B* 113, 3572-3578 (2009).
10. Bacri, L. et al. Discrimination of neutral oligosaccharides through a nanopore. *Biochem. Biophys. Res. Commun.* 412, 561-564 (2011).
11. Movileanu, L., Schmittschmitt, J. P., Scholtz, J. M. & Bayley, H. Interactions of peptides with a protein pore. *Biophys. J.* 89, 1030-1045 (2005).
12. Mohammad, M. M., Prakash, S., Matouschek, A. & Movileanu, L. Controlling a single protein in a nanopore through electrostatic traps. *J. Am. Chem. Soc.* 130, 4081-4088 (2008).
13. Piguet, F. et al. Identification of single amino acid differences in uniformly charged homopolymeric peptides with aerolysin nanopore. *Nat. Commun.* 9, (2018).
14. Lamichhane, U. et al. Peptide translocation through the mesoscopic channel: Binding kinetics at the single molecule level. *Eur. Biophys. J.* 42, 363-369 (2013).
15. Stefureac, R., Long, Y. T., Kraatz, H. B., Howard, P. & Lee, J. S. Transport of α-helical peptides through α-hemolysin and aerolysin pores. *Biochemistry* 45, 9172-9179 (2006).
16. Chavis, A. E. et al. Single Molecule Nanopore Spectrometry for Peptide Detection. *ACS Sensors* 2, 1319-1328 (2017).
17. Maglia, G., Restrepo, M. R., Mikhailova, E. & Bayley, H. Enhanced translocation of single DNA molecules through-hemolysin nanopores by manipulation of internal charge. *Proc. Natl. Acad. Sci.* 105, 19720-19725 (2008).
18. Stoddart, D., Heron, A. J., Mikhailova, E., Maglia, G. & Bayley, H. Single-nucleotide discrimination in immobilized DNA oligonucleotides with a biological nanopore. *Proc. Natl. Acad. Sci.* 106, 7702-7707 (2009).
19. Boersma, A. J. & Bayley, H. Continuous stochastic detection of amino acid enantiomers with a protein nanopore. *Angew. Chemie—Int. Ed.* 51, 9606-9609 (2012).
20. Stoddart, D. et al. Nucleobase recognition in ssDNA at the central constriction of the hemolysin pore. *Nano Lett.* 10, 3633-3637 (2010).
21. Kennedy, E., Dong, Z., Tennant, C. & Timp, G. Reading the primary structure of a protein with 0.07 nm 3 resolution using a subnanometre-diameter pore. *Nat. Nanotechnol.* 11, 968-976 (2016).
22. Li, S., Cao, C., Yang, J. & Long, Y. Detection of Peptides with Different Charges and Lengths by Using the Aerolysin Nanopore. 4, 1-5 (2018).
23. Asandei, A. et al. Electroosmotic Trap Against the Electrophoretic Force Near a Protein Nanopore Reveals Peptide Dynamics during Capture and Translocation. *ACS Appl. Mater. Interfaces* 8, 13166-13179 (2016).
24. Chinappi, M. & Cecconi, F. Protein sequencing via nanopore based devices: a nanofluidics perspective. *J. Phys. Condens. Matter* in press, (2018).
25. Tanaka, K., Caaveiro, J. M. M., Morante, K., Gonzilez-Manãs, J. M. & Tsumoto, K. Structural basis for self-assembly of a cytolytic pore lined by protein and lipid. *Nat. Commun.* 6, 4-6 (2015).
26. Wloka, C., Mutter, N. L., Soskine, M. & Maglia, G. Alpha-Helical Fragaceatoxin C Nanopore Engineered for Double-Stranded and Single-Stranded Nucleic Acid Analysis. *Angew. Chemie—Int. Ed.* 55, 12494-12498 (2016).

27. Huang, G., Willems, K., Soskine, M., Wloka, C. & Maglia, G. Electro-osmotic capture and ionic discrimination of peptide and protein biomarkers with FraC nanopores. *Nat. Commun.* 8, 1-13 (2017).
28. Soskine, M., Biesemans, A., De Maeyer, M. & Maglia, G. Tuning the size and properties of ClyA nanopores assisted by directed evolution. *J. Am. Chem. Soc.* 135, 13456-13463 (2013).
29. Aqvist, J. et al. Dipoles Localized at Helix Termini of Proteins Stabilize Charges. *Proc. Natl. Acad. Sci.* 88, 2026-2030 (1991).
30. Rincon-Restrepo, M., Mikhailova, E., Bayley, H. & Maglia, G. Controlled translocation of individual DNA molecules through protein nanopores with engineered molecular brakes. *Nano Lett.* 11, 746-750 (2011).
31. Wanunu, M., Sutin, J., McNally, B., Chow, A. & Meller, A. DNA translocation governed by interactions with solid-state nanopores. *Biophys. J.* 95, 4716-4725 (2008).
32. Biesemans, A., Soskine, M. & Maglia, G. A Protein Rotaxane Controls the Translocation of Proteins Across a ClyA Nanopore. *Nano Lett.* 15, 6076-6081 (2015).
33. Ho, C. W. et al. Engineering a nanopore with co-chaperonin function. *Sci. Adv.* 1, 1-9 (2015).
34. Wanunu, M., Morrison, W., Rabin, Y., Grosberg, A. Y. & Meller, A. Electrostatic focusing of unlabelled DNA into nanoscale pores using a salt gradient. *Nat. Nanotechnol.* 5, 160-165 (2010).
35. Stoddart, D., Franceschini, L., Heron, A., Bayley, H. & Maglia, G. DNA stretching and optimization of nucleobase recognition in enzymatic nanopore sequencing. *Nanotechnology* 26, 10-16 (2015).
36. Stryer, L. Biochemistry. *Biochemistry* (4th ed.) (1995).
37. Soskine, M., Biesemans, A. & Maglia, G. Single-molecule analyte recognition with ClyA nanopores equipped with internal protein adaptors. *J. Am. Chem. Soc.* 137, 5793-5797 (2015).
38. Andre, I., Bradley, P., Wang, C. & Baker, D. Prediction of the structure of symmetrical protein assemblies. *Proc. Natl. Acad. Sci.* 104, 17656-17661 (2007).

The invention claimed is:

1. A system comprising oligomeric Fragaceatoxin C (FraC) nanopores disposed in a lipid bilayer, wherein a sum of a first number of nanopores in a heptameric (Type II) state and a second number of nanopores in a hexameric (Type III) state is at least 60% of a total number of the oligomeric FraC nanopores.

2. The system of claim 1, wherein the sum of the first number of nanopores in the heptameric (Type II) state and the second number of nanopores in the hexameric (Type III) state is at least 65% of the total number of the oligomeric FraC nanopores.

3. The system of claim 1, wherein the first number of nanopores in the heptameric (Type II) state is at least 60% of the total number of the oligomeric FraC.

4. The system of claim 1, wherein the second number of nanopores in the hexameric (Type III) state is at least 60% of the total number of the oligomeric FraC nanopores.

5. The system of claim 1, wherein the oligomeric FraC nanopores comprise mutant FraC monomers comprising a mutation at position W112 or W116.

6. The system of claim 5, wherein said mutation comprises a substitution of a tryptophan (W) with a serine (S), a threonine (T), an alanine (A), an asparagine (N), a glutamine (Q) or a glycine (G).

7. The system of claim 5, wherein said mutant FraC monomers comprise mutation W112S or W116S.

8. The system of claim 7, wherein the mutant FraC monomers comprise mutations (a) W112S and W116S, (b) D109S and W116S, or (c) D10C and W116S.

9. The system of claim 1, wherein the oligomeric FraC nanopores comprise mutant FraC monomers comprising a mutation at position D109.

10. The system of claim 9, wherein the mutant FraC monomers comprise mutation D109S or D109T.

11. The system of claim 1, wherein the system is operative to detect a property of an analyte by subjecting the oligomeric FraC nanopores to an electric field such that the analyte electrophoretically or electro-osmotically translocates through a nanopore of the oligomeric FraC nanopores.

12. The system of claim 11, wherein the analyte is a peptide.

13. A method for providing the system of claim 1, comprising:
  (i) providing recombinant FraC monomers;
  (ii) contacting said recombinant FraC monomers with liposomes to assemble the recombinant FraC monomers into oligomers;
  (iii) recovering the oligomers from the liposomes; and
  (iv) contacting the oligomers with the lipid bilayer to allow formation of the oligomeric FraC nanopores.

14. The method of claim 13, further comprising isolating the first number of nanopores in the heptameric (Type II) state and the second number of nanopores in the hexameric (Type III) state.

15. A method of performing peptide analysis, the method comprising
  (a) providing the system of claim 1 and a solution comprising a peptide for analysis, wherein the solution is disposed on one side of the lipid bilayer; and
  (b) subjecting a nanopore of the oligomeric FraC nanopores to an electric field such that the peptide electrophoretically or electro-osmotically translocates through the nanopore.

16. The method of claim 15, wherein the system is integrated in a portable device comprising a plurality of individual systems.

17. A method of performing single molecule detection, the method comprising:
  (a) providing the system of claim 1 and a solution comprising a plurality of single molecules, wherein the solution is disposed on one side of the lipid bilayer;
  (b) subjecting a nanopore of the oligomeric FraC nanopores to an electric field such that a single molecule of the plurality of single molecules electrophoretically or electro-osmotically translocates through the nanopore; and
  (c) detecting the single molecule translocated through the nanopore.

18. The system of claim 1, wherein a Type II FraC nanopore in the first number of nanopores has (i) a conductance from about 50% to about 68% of a conductance of a Type I FraC nanopore when assayed at pH 7.5 in a 1M NaCl solution, or (ii) a conductance from about 41% to about 62% of the conductance of the Type I FraC nanopore when assayed at pH 4.5 in a 1M KCl solution.

19. The system of claim 18, wherein a Type III FraC nanopore in the second number of nanopores has a conductance from about 16% to about 24% of the conductance of the Type I FraC nanopore when assayed at pH 4.5 in a 1M KCl solution.

20. The system of claim 1, wherein a Type II FraC nanopore in the first number of nanopores or a Type III FraC nanopore in the second number of nanopores comprises a monomer comprising an amino acid sequence as set forth in SEQ ID NO: 1.

21. The system of claim 1, wherein a Type II FraC nanopore in the first number of nanopores or a Type III FraC nanopore in the second number of nanopores comprises a monomer comprising an engineered variation of an amino acid sequence as set forth in SEQ ID NO: 1.

22. The system of claim 21, wherein the engineered variation comprises a mutant sequence comprising a mutation at positions 109, 112, or 116 when aligned to the amino acid sequence as set forth in SEQ ID NO: 1.

23. The system of claim 22, wherein the mutation comprises a substitution of aspartic acid (D) with an uncharged amino acid residue.

24. The system of claim 1, wherein the system further comprises a first electrode on a first side of the lipid bilayer and a second electrode on a second side of the lipid bilayer.

* * * * *

UNITED STATES PATENT AND TRADEMARK OFFICE
CERTIFICATE OF CORRECTION

| | |
|---|---|
| PATENT NO. | : 12,105,079 B2 |
| APPLICATION NO. | : 17/269771 |
| DATED | : October 1, 2024 |
| INVENTOR(S) | : Huang et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 799 days.

Signed and Sealed this
Twelfth Day of August, 2025

Coke Morgan Stewart
*Acting Director of the United States Patent and Trademark Office*